United States Patent
Viglianti et al.

(10) Patent No.: US 7,672,704 B2
(45) Date of Patent: Mar. 2, 2010

(54) METHODS AND COMPOSITIONS FOR BLOOD POOL IDENTIFICATION, DRUG DISTRIBUTION QUANTIFICATION AND DRUG RELEASE VERIFICATION

(75) Inventors: Benjamin L. Viglianti, Durham, NC (US); Mark W. Dewhirst, Durham, NC (US); James R. MacFall, Graham, NC (US); Zeljko Vujaskovic, Chapel Hill, NC (US)

(73) Assignee: Duke University, Durham, NC (US)

( * ) Notice: Subject to any disclaimer, the term of this patent is extended or adjusted under 35 U.S.C. 154(b) by 1366 days.

(21) Appl. No.: 10/661,977

(22) Filed: Sep. 11, 2003

(65) Prior Publication Data

US 2004/0101969 A1   May 27, 2004

Related U.S. Application Data

(60) Provisional application No. 60/409,899, filed on Sep. 11, 2002, provisional application No. 60/415,591, filed on Oct. 2, 2002.

(51) Int. Cl.
*A61B 5/055* (2006.01)
(52) U.S. Cl. .................... 600/407; 424/450; 424/9.321; 600/410
(58) Field of Classification Search ............. 424/9.321, 424/9.3, 9.36, 450, 9.51, 9.52; 600/420, 600/431
See application file for complete search history.

(56) References Cited

U.S. PATENT DOCUMENTS

| | | | |
|---|---|---|---|
| 4,728,575 A * | 3/1988 | Gamble et al. ............ 424/9.321 |
| 5,149,319 A * | 9/1992 | Unger ........................ 604/22 |
| 5,260,050 A | 11/1993 | Ranney | |
| 5,387,410 A | 2/1995 | Bosworth et al. ............... 424/9 |
| 5,411,730 A * | 5/1995 | Kirpotin et al. .......... 424/9.322 |
| 5,542,935 A * | 8/1996 | Unger et al. ................. 604/190 |
| 5,665,383 A * | 9/1997 | Grinstaff et al. ............. 424/450 |
| 5,810,888 A * | 9/1998 | Fenn ......................... 607/154 |
| 6,200,598 B1 * | 3/2001 | Needham .................... 424/450 |
| 6,207,133 B1 | 3/2001 | Reszka et al. ............ 424/9.321 |
| 6,231,834 B1 * | 5/2001 | Unger et al. ............... 424/9.51 |
| 6,258,378 B1 * | 7/2001 | Schneider et al. ........... 424/450 |

(Continued)

FOREIGN PATENT DOCUMENTS

WO    WO9844910    * 10/1998

OTHER PUBLICATIONS

International Search Report for corresponding PCT Application No. PCT/US03/28674 dated May 23, 2005.

(Continued)

*Primary Examiner*—Brian Casler
*Assistant Examiner*—Elmer Chao
(74) *Attorney, Agent, or Firm*—Jenkins, Wilson, Taylor & Hunt, P.A.

(57) ABSTRACT

Methods and compositions useful for detecting an in vivo blood pool, monitoring the distribution of a compound of interest to a desired site in an organism by magnetic resonance imaging, monitoring the accumulation of a compound of interest at a desired site in vivo by magnetic resonance imaging, and monitoring the release of liposomal contents to an external stimulus at a desired site in vivo by magnetic resonance imaging are disclosed. Some compositions comprise envirosensitive or non-sensitive liposomes. Contrast agents, such as manganese-based compounds, are also disclosed.

26 Claims, 15 Drawing Sheets

U.S. PATENT DOCUMENTS

| | | | |
|---|---|---|---|
| 6,261,537 | B1 | 7/2001 | Klaveness et al. |
| 6,468,505 | B1 * | 10/2002 | Lang et al. ............... 424/9.321 |
| 6,802,813 | B2 | 10/2004 | Schutt |
| 2004/0101959 | A1 | 5/2004 | Viglianti et al. |
| 2004/0115186 | A1 | 6/2004 | Segal et al. |
| 2005/0136002 | A1 | 6/2005 | Fossheim et al. |

OTHER PUBLICATIONS

Cheung et al., Lodading of doxorubicin into liposomes by forming $Mn^{2+}$-drug complexes, *Biochimica et Biophysica Acta* 1414:205-216 (1998).

Fossheim et al., Paramagnetic liposomes as MRI contrast agents: influence of liposomal physicochemical properties on the in vitro relaxivity, *Magnetic Resonance Imaging* 17(1):83-89 (1999).

Artemov et al., Magnetic Resonance Pharmacoangiography to Detect and Predict Chemotherapy Delivery to Solid Tumors, *Cancer Research* 61:3039-3044 (2001).

Suga et al., Potential of Gd-DTPA-Mannan Liposome Particles as a Pulmonary Perfusion MRI Contrast Agent, *Investigative Radiology* 36(3):136-145 (Mar. 2001).

Bondurant et al., Photoinitiated destabilization of sterically stabilized liposomes, *Biochimica et Biophysica Acta* 1511:113-122 (2001).

Clapp et al., Two-Dimensional Polymerization of Lipid Bilayers: Visible-Light-Sensitized Photoinitiation, *Macromolecules* 30:32-41 (1997).

de Oliveira, et al., pH-sensitive liposomes as a carrier for oligonucleotides: a physico-chemical study of the interaction between DOPE and a 15-mer oligonucleotide in excess water, *Biophys Chem* 87(203):127-137 (2000).

Morgan et al., Use of photosensitive, antibody directed liposomes to destroy target populations of cells in bone marrow: a potential purging method for autologous bone marrow transplantation, *Br. J. Cancer* 65(1):58-64 (1992).

Ziegler et al., Investigation of lipid peroxidation in liposomes induced by heavy ion irradiation, *Radiat Environ Biophys* 37(2):95-100 (1998).

Dewhirst et al., Hyperthermia, Chapter 41, Section 9, *Radiation Oncology*.

Fossheim et al., Paramagnetic Liposomes as MRI Contrast Agents: Influence of Liposomal Physicochemical Properties on the Vitro Relaxivity, *Magnetic Resonance Imaging* 17(1):83-89 (1999).

Gaber et al., Thermosensitive Liposomes: Extravasation and Release of Contents in Tumor Microvascular Networks, *Int. J. Radiation Oncology Biol. Phys.* 36(5):1177-1187 (1996).

Løking et al., pH-Sensitive paramagnetic liposomes for MRI: assessment of stability in blood, *Magnetic Resonance Imaging* 21:531-540 (2003).

Løking et al., pH-sensitive paramagnetic liposomes as MRI contrast agents: in vitro feasibility studies, *Magnetic Resonance Imaging* 19:731-738 (2001).

Mayer et al., Uptake of Dibucaine into Large Unilamellar Vesicles in Response to a Membrane Potential, *J. of Biological Chemistry* 260(2):802-808 (Jan. 25, 1985).

Maruyama et al., Enhanced Delivery of Dixorubicin to Tumor by Long-circulating Thermosensitive Liposomes and Local Hyperthermia, *Biochimica et Biophysica Acta* 1149(2):209-216 (Jul. 4, 1993) (ABSTRACT).

Webb et al., In-vivo NMR thermometry with liposomes containing 59Co complexes, *Int. J. Hyperthermia* 11(6):821-827 (1995) (ABSTRACT).

Mueller et al., Visible-Light-Stimulated Destabilization of PEG-Liposomes, *Macromolecules* 33:4799-4804 (2000).

Needham and Dewhirst, The development and testing of a new temperature-sensitive drug delivery system for the treatment of solid tumors, *Advanced Drug Delivery Reviews* 53:285-305 (2001).

Spratt et al., Rapid release of liposomal contents upon photoinitiated destabilization with UV exposure, *Biochimica et Biophysica Acta* 1611:35-43 (2003).

Invitation to Pay Additional Fees and, Where Applicable, Protest Fee for International Application No. PCT/US 07/26493 dated Apr. 9, 2008.

Rubesova et al., "Gd-Labeled Liposomes for Monitoring Liposome-encapsulated Chemotherapy: Quantification of Regional Update in Tumor and Effect on Drug Delivery," *Acad. Radiol.*, vol. 9 (Suppl. 2), pp. S525-S527 (2002).

Notification of Transmittal of International Search Report and the Written Opinion of the International Searching Authority, or the Declaration corresponding to International Application No. PCT/US 07/26493 dated Jun. 27, 2008.

Office Communication corresponding to U.S. Appl. No. 11/648,148 dated Jan. 30, 2009.

* cited by examiner

METHODS AND COMPOSITIONS FOR BLOOD POOL IDENTIFICATION, DRUG DISTRIBUTION QUANTIFICATION AND DRUG RELEASE VERIFICATION

CROSS REFERENCE TO RELATED APPLICATIONS

This application claims the benefit of U.S. Provisional Patent Application Ser. Nos. 60/409,899 filed Sep. 11, 2002 and 60/415,591 filed Oct. 2, 2002; the disclosures of each of which are incorporated herein by reference in their entireties.

GRANT STATEMENT

This invention was made with federal grant money under NCI grants CA42745 and R24 CA92656. Thus, the United States Government has certain rights in the present invention.

TECHNICAL FIELD

The methods and compositions disclosed herein generally relate to employing magnetic resonance techniques to monitor drug delivery in vivo. More particularly, the disclosure relates to the use of liposomes encapsulating a drug and a contrast agent to monitor drug delivery to a desired site in vivo by magnetic resonance imaging techniques. The disclosure further relates to blood pool agents, adapted to provide imaging of a site over an extended period of time.

| Abbreviations | |
|---|---|
| AP | alkaline phosphatase |
| CT | computerized tomography |
| DOX | doxorubicin |
| ESR | electron spin resonance |
| HEPES | N-2-Hydroxyethylpiperazine-N'-2 ethanesulfonic acid |
| HT | hyperthermia |
| LTSL | low temperature sensitive (thermosensitive) liposomes |
| MLV | multilamellar vesicle |
| MR | magnetic resonance |
| MRI | magnetic resonance imaging |
| MUGA | multiple-gated arteriography |
| NMR | nuclear magnetic resonance |
| NTSL | non-temperature sensitive (non-thermally sensitive) liposomes |
| PET | positron emission tomography |
| RES | reticuloendothelial system |
| RF | radio frequency |
| SNR | signal-to-noise ratio |
| TCA | trichloroacetic acid |
| Te | echo time |
| TI | time of inversion |
| $T_m$ | melting (phase transition) temperature |
| $T_r$ | repetition time |
| $T_1$ | spin lattice relaxation time |
| $T_2$ | spin-spin relaxation time |

BACKGROUND ART

Medical diagnostic imaging has evolved as an important non-invasive tool for the evaluation of pathological and physiological processes. Presently, nuclear magnetic resonance imaging ("MRI") and computerized tomography ("CT") are two of the most widely used imaging modalities. Although both MRI and CT can be performed without the administration of contrast agents, the ability of many contrast enhancement agents to enhance the visualization of internal tissues and organs has resulted in their widespread use.

Proton MRI is based on the principle that the concentration and relaxation characteristics of protons in tissues and organs can influence the intensity of a magnetic resonance image. Contrast enhancement agents that are useful for proton MRI effect a change in the relaxation characteristics of protons, which can result in image enhancement and improved soft-tissue differentiation. Different classes of proton MR imaging agents include paramagnetic metal chelates and nitroxyl spin labeled compounds.

Detection and monitoring of tumor growth and remission is vital for the effective diagnosis and treatment of cancer. Current methods for detecting tumor growth and regression using CT scan, positron emission tomography ("PET"), optical imaging and MRI are limited in their ability to distinguish between normal and tumor tissue. Additionally, the ability to image the vasculature within in a tissue and occlusion of that vasculature finds application in a variety of different scenarios. Vascular occlusion imaging is presently limited by a variety of obstacles, one of which is the inability to selectively image occlusions over other tissues and structures. Further, there is no currently available method of monitoring internal wound healing, nor is there an adequate method of monitoring angiogenic activity in tumor and non-tumor tissue.

The use of envirosensitive liposomes in hyperthermia therapy is a promising approach to targeting a tumor or other tissue. Broadly, envirosensitive liposomes comprise a formulation adapted to lose structural integrity under certain environmental conditions. For example, thermosensitive liposomes lose structural integrity within a given temperature range. Alternatively, the envirosensitive liposome can be a radiation sensitive liposome, which is formulated to lose its structural integrity when contacted with a particular wavelength range of electromagnetic radiation. When an envirosensitive liposome, such as a thermosensitive or a radiation sensitive liposome, loses its structural integrity, the contents of the liposome are released.

One consideration with respect to the use of envirosensitive liposomes as a delivery vehicle (e.g. for a therapeutic compound) is the ability to target the liposomes to a desired location, such as a tumor. Targeting liposomes, both envirosensitive and insensitive species, has been a subject of research for some time. Various approaches have been taken, including the formation of immunoliposomes, which comprise, for example, an antibody or a fragment of an antibody (see, e.g., Sullivan & Huang, (1985) *Biochim. Biophys. Acta* 812(1): 116-126; Perlaky et al., (1996) *Oncol. Res.* 8(9): 363-369).

Liposome targeting, however, depends in part on how stably the liposomes administered to a subject circulate through the circulatory system in the normal physiological environment and how effectively the liposomes release their content (e.g. a drug) at a particular desired site (e.g. a tumor). In the case of some thermosensitive liposomes targeting has been problematic. For example, the liposomes described by Yatvin et al. (Yatvin et al., (1978) *Science* 202: 1290) release only a small amount of the drug at the temperature of hyperthermia. Other liposomes have been observed to release the drug at a temperature lower (e.g., 37-39° C.) than that typically reached in an approach employing hyperthermia (Bassett et al., (1986) *J. Urol.* 135(3): 612-615; Needham et al., (2000) *Cancer Res.* 60(5): 1197-1201).

However, an approach for monitoring the release of liposome contents once an envirosensitive liposome has lost structural integrity has not been disclosed in the art. Therefore, absent a method of monitoring liposome opening and content release, a clinician or researcher must assume that the liposome was delivered to the desired site, that it ruptured and released its contents and that the contents were delivered to the desired site.

Thus, what is needed is an envirosensitive liposome, for example a thermosensitive liposome composition that exhibits a desirable phase transition at the typical temperature of hyperthermia (40-45° C.), or a radiation sensitive liposome that exhibits a desirable phase transition when contacted by a particular wavelength range of electromagnetic radiation. Further, what is needed is an envirosensitive liposome that is adapted to entrap a drug at a high concentration for long periods of time when maintained at physiological conditions, for example a temperature lower than that of hyperthermia for thermosensitive liposomes, and that is adapted to release the drug efficiently in a very short time after a particular environmental stimulation, for example at the temperature of hyperthermia or higher for thermosensitive liposomes. Such an envirosensitive liposome composition would also be adapted to be tracked to a desired location, wherein content delivery could be monitored in vivo by a non-invasive method.

What is also needed is a non-invasive method of monitoring tumor growth or regression, vascular morphology, vascular occlusion formation and dissolution, angiogenesis and wound healing in a subject that offers superior sensitivity, relative to the currently available methods. These and other problems are addressed by the compositions and methods disclosed herein.

SUMMARY OF THE INVENTION

In one aspect of the presently disclosed methods and compositions, a method of monitoring the accumulation of a compound of interest at a desired site in vivo by magnetic resonance imaging is disclosed. In one embodiment, the method comprises: (a) administering to a subject a non-sensitive liposome composition comprising: (i) a contrast agent; (ii) a compound of interest; and (iii) a non-sensitive liposome encapsulating the contrast agent and the compound of interest; and (b) monitoring the accumulation of the compound of interest at the site of interest by magnetic resonance imaging. In one embodiment, the method comprises increasing blood flow to the desired site. Increasing the blood flow can comprise mechanical stimulation, ultrasound therapy and/or heating the desired site.

In another aspect of the presently disclosed methods and compositions, an in vivo method of monitoring the localization and distribution of a compound of interest to a desired site in an organism by magnetic resonance imaging is disclosed. In one embodiment, the method comprises: (a) administering an envirosensitive liposome composition to the subject, the composition comprising: (i) a contrast agent; (ii) a compound of interest; and (iii) an envirosensitive liposome encapsulating the contrast agent and the compound of interest; and (c) monitoring the distribution of the compound of interest to the desired site by magnetic resonance imaging. In one embodiment, the method comprises increasing blood flow to the desired site.

In yet another aspect, a method of detecting an in vivo blood pool is disclosed. In one embodiment, the method comprises: (a) administering a liposome composition to a subject, the composition comprising: (i) a contrast agent; and (ii) a liposome encapsulating the contrast agent; (b) generating a magnetic resonance image of a site of interest; and (c) detecting the presence of an in vivo blood pool by analyzing the magnetic resonance image.

In a further aspect, a method of monitoring the accumulation of a compound of interest at a desired site in vivo by magnetic resonance imaging is disclosed. In one embodiment, the method comprises: (a) administering to a subject an envirosensitive liposome composition comprising: (i) a contrast agent; (ii) a compound of interest; and (iii) an envirosensitive liposome encapsulating the contrast agent and the compound of interest; and (b) monitoring the accumulation of the compound of interest at a desired site by magnetic resonance imaging.

In another aspect, a method of generating a heating profile of a site of interest is disclosed. In one embodiment, the method comprises: (a) administering to a subject a thermosensitive liposome composition comprising: (i) a contrast agent; and (ii) a thermosensitive liposome encapsulating the contrast agent and the compound of interest and having a melting temperature $T_m$; (b) heating a site of interest in a subject; (c) monitoring release of the contrast agent from the thermosensitive liposome using magnetic resonance imaging; and (d) generating a heating profile of the site of interest, wherein heating of an area to a temperature of at least $T_m$ is indicated by release of contrast agent, preferably at a periphery of the area.

In the methods disclosed herein, heating can be, for example, by a method selected from the group consisting of contacting a heated material with the site of interest, applying electromagnetic energy that heats the desired site, such as, for example microwave or radio frequency energy to the site, applying ultrasonic energy to the site and applying a laser beam to the site. A site of interest can be selected from the group consisting of, for example, a tumor, injury site, and tissue edema.

In the methods disclosed herein, an envirosensitive liposome can comprise, for example, a thermosensitive liposome, a pH-sensitive liposome, a chemosensitive liposome and a radiation-sensitive liposome.

In the methods disclosed herein, a non-sensitive liposome can comprise, for example, DSPC/Cholesterol (55:45, mol:mol). A thermosensitive liposome can comprise, for example, a formulation selected from the group consisting of DPPC-$PEG_{2000}$, DPPC-DSPE-$PEG_{2000}$ (95:5, mol:mol); DPPC-MSPC-DSPE-$PEG_{2000}$ (90:10:4, mol:mol).

In the methods disclosed herein, a contrast agent can be any paramagnetic compound. For example, a contrast agent can comprise a element selected from the group consisting of Gd, Cu, Cr, Fe, Co, Er, Ni, Eu, Dy, Zn, Mg, Mo, Li, Ta, and Mn.

In the methods disclosed herein, various compounds of interest can be employed in the methods of the present invention, and a compound of interest can be, for example, a chemotherapeutic agent.

Accordingly, it is an object to provide a method of monitoring the localization and/or distribution of a compound of interest at a desired site in vivo by magnetic resonance imaging. This and other objects are achieved in whole or in part by the presently disclosed methods and compositions.

An object of the disclosure having been stated hereinabove, other objects will be evident as the description proceeds, when taken in connection with the accompanying Examples and Drawings as best described hereinbelow.

DETAILED DESCRIPTION

I. Definitions

Figure 1A:
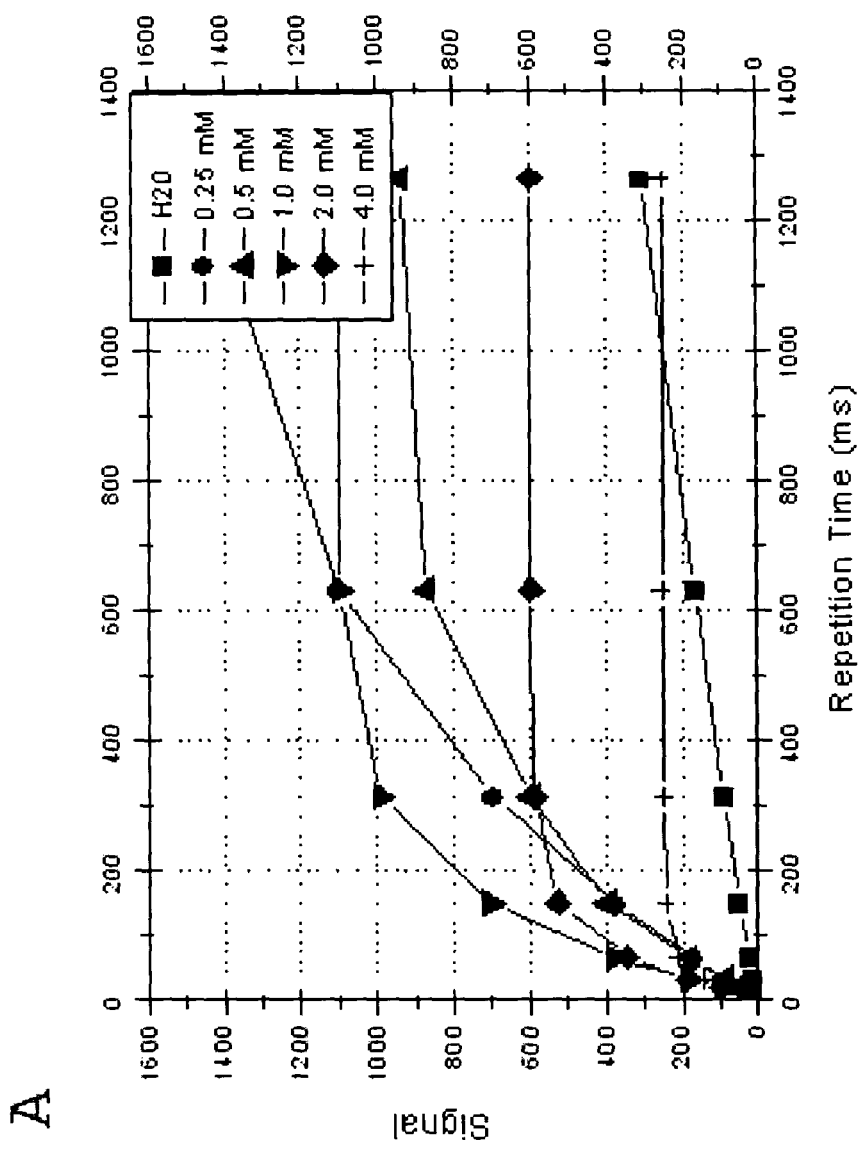
FIG. 1A is a plot depicting the dependency of signal on $T_r$ for a non-sensitive liposome-DOX-$MnSO_4$ (temperature=29.93° C.) formulation at various concentrations. In this plot, solid squares represent water alone, circles represent formulations comprising 0.25 mM DOX, solid triangles represent formulations comprising 0.5 mM DOX, solid inverted triangles represent formulations comprising 1.0 mM DOX, solid diamonds represent formulations comprising 2.0 mM DOX and crosses represent formulations comprising 4.0 mM DOX.

Following long-standing patent law convention, the terms "a" and "an" mean "one or more" when used in this disclosure, including the claims.

As used herein, the term "about", when referring to a value or to an amount of mass, weight, time, volume, concentration or percentage is meant to encompass variations of ±20% or ±10%, more preferably ±5%, even more preferably ±1%, and still more preferably ±0.1% from the specified amount, as such variations are appropriate to perform the disclosed method.

As used herein, the term "blood pool" means a localized volume of blood. A blood pool can arise from a normally occurring phenomenon, such as pooling of blood in a subject's heart. A blood pool can also arise from an unnatural vascular condition, such as an aneurysm. The blood in a blood pool can be circulating, prevented from circulating or circulating to some degree. Generally, then, a blood pool is a localized concentration of blood, and a blood pool can comprise any volume of blood.

As used herein, the term "detecting" means confirming the presence of a target entity (which can be a biological structure, such as a vascular blockage, vascular damage or an occlusion) by observing the occurrence of a detectable signal, such as a radiologic or spectroscopic signal or a feature of an image generated by magnetic resonance that will appear exclusively in the presence of the target entity.

As used herein, the term "envirosensitive liposome" means a liposome formulated using physiologically compatible constituents, such as, but not limited to, dipalmitoylphosphatidyl-choline and dipalmitoylphosphatidyl-glycerol phospholipids, which permit preparation of liposomes using art-recognized techniques that are formulated to lose structural integrity and release their contents under specific environmental conditions. The specific environmental conditions under which a particular envirosensitive liposome loses its structural integrity are variable and dependent upon the formulation of the particular liposome. Typically, the environmental conditions differ from normal physiological conditions. For example, thermosensitive liposomes can be formulated to release their contents at temperatures higher than normal mammalian body temperature. Alternatively, radiation-sensitive liposomes can be formulated to release their contents when they interact with electromagnetic radiation within a particular wavelength range, such as x-rays, or other ionizing radiation. While these examples are both categorized as envirosensitive liposomes, as the term is used herein, they are not necessarily structurally vulnerable to the same environmental conditions. For example, a thermosensitive liposome may not lose structural integrity when contacting x-rays, and vice versa for a radiation-sensitive liposome held at a particular temperature. However, envirosensitive liposomes having overlapping environmental sensitivities, for example thermal and pH sensitivities, can also be formulated, and are included within the term "envirosensitive liposome," as used herein. One of skill in the art will readily recognize and be able to formulate without undue experimentation other types of envirosensitive liposomes, and these formulation are also encompassed by the term as used herein. Non-limiting examples of envirosensitive liposomes include thermosensitive liposomes, radiation-sensitive liposomes, pH-sensitive liposomes, acoustic (e.g. ultrasound)-sensitive liposomes, antigen-sensitive liposomes (e.g. liposomes having recognition molecules, for example, antibodies or antibody fragments (see, e.g., Sullivan & Huang, (1985) *Biochim. Biophys. Acta* 812(1): 116-126; Perlaky et al., (1996) *Oncol. Res.* 8(9): 363-369), incorporated into the membrane such that contact of the recognition molecule with its antigen results in loss of structural integrity of the liposome through, for example, a conformational change in the recognition molecule) and chemosensitive liposomes (e.g. liposomes sensitive to particular chemical agents). The present disclosure encompasses the use of envirosensitive liposomes that are less than about 400 nm in diameter, such as, for example liposomes having a diameter of about 200 nm or about 120 nm in diameter to facilitate handling, administration, unhindered progress through mammalian vasculature, and minimize side effects, e.g., interference with the mammalian blood clotting cascade. As used herein, the term "hyperthermia" means the elevation of the temperature of a subject's body, or a part of a subject's body, compared to the basal temperature of the subject. Such elevation can be the result of a natural process (such as inflammation) or artificially induced for therapeutic or diagnostic purposes. In mammals, a basal body temperature is ordinarily maintained due to the thermoregulatory center in the anterior hypothalamus, which acts to balance heat production by body tissues with heat loss. "Hyperthermia" refers to the elevation of body temperature above the hypothalamic set point due to insufficient heat dissipation. In contrast to hyperthermia, "fever" refers to a systemic elevation of body temperature due to a change in the thermoregulatory center. The overall mean oral temperature for a healthy human aged 18-40 years is 36.8.±0.4° C. (98.2±0.7° F.). See, e.g., *Harrison's Principles of Internal Medicine* (Fauci et al., eds.) 14th Ed. McGraw-Hill, New York, p. 84 (1998).

As used herein, the term "inner transition elements" means those elements known as lanthanide (or rare earth) and actinide elements. Inner transition elements are also known as f-block transition elements.

As used herein, the term "liposome" means a generally spherical cluster or aggregate of amphipathic compounds, including lipid compounds, typically in the form of one or more concentric layers, for example, bilayers.

As used herein, the term "radiation-sensitive liposome" means a liposome formulated using physiologically compatible constituents, such as, but not limited to, dipalmitoylphosphatidyl-choline and dipalmitoylphosphatidyl-glycerol phospholipids, which permit preparation of liposomes using art-recognized techniques that are formulated to lose structural integrity and release their contents when interacting with electromagnetic radiation having a specific wavelength range. The specific wavelength range under which a particular radiation-sensitive liposome loses its structural integrity is variable and dependent upon the formulation of the particular liposome. For the purposes of example but not limitation, a liposome can be formulated to lose structural integrity and release its contents when interacting with x-rays, that is electromagnetic radiation having a wavelength in the range of about $1 \times 10^{-11}$ m to about $1 \times 10^{-8}$ m, but not when interacting with radiation having a greater or lesser wavelength. In other embodiments, the wavelength sensitivity may include a different range, or encompass x-rays in a broader range, such as, for example broad sensitivity to all ionizing radiation. The present disclosure encompasses the use of radiation-sensitive liposomes that are less than about 400 nm in diameter, such as, for example liposomes having a diameter of about 200 nm or about 120 nm in diameter to facilitate handling, administration, unhindered progress through mammalian vasculature, and minimize side effects, e.g., interference with the mammalian blood clotting cascade.

As used herein, the term "relaxivity" means the slope of the line drawn between points on a plot of $1/T_1$ or $1/T_2$ against contrast agent concentration.

As used herein, the term "subject" means any organism. The term need not refer exclusively to human beings, which is one example of a subject, but can also refer to animals such as mice, rats, dogs, poultry, and *Drosophila* and even tissue cultures. The methods disclosed herein are particularly useful in the treatment and diagnosis of warm-blooded vertebrates. Thus, the disclosure concerns mammals and birds. More particularly, provided is the treatment and/or diagnosis of mammals such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also provided is the treatment of birds, including the treatment of those kinds of birds that are endangered, kept in zoos, as well as fowl, and more particularly domesticated fowl, e.g., poultry, such as turkeys, chickens, ducks, geese, guinea fowl, and the like, as they are also of economical importance to humans. Thus, provided is the treatment of livestock, including, but not limited to, domesticated swine (pigs and hogs), ruminants, horses, poultry, and the like.

As used herein, the term "$T_1$" means longitudinal relaxation time, and is also known as the spin lattice relaxation time ($1/T_1$ is a rate constant, $R_1$, the spin-lattice relaxation rate constant).

As used herein, the term "$T_2$" means transverse relaxation time, which arises, in part, from spin-spin relaxation mechanisms. $1/T_2$ is also a rate constant, $R_2$, the spin-spin relaxation rate constant.

As used herein, the term "non-sensitive liposome" means a liposome formulated using physiologically compatible constituents, such as dipalmitoylphosphatidyl-choline and dipalmitoylphosphatidyl-glycerol phospholipids and cholesterol, that permits preparation of liposomes using art-recognized techniques that do not release their contents as a result of specific environmental stimulation, such as hyperthermic conditions, pH variance, or interaction with electromagnetic radiation. For example, in contrast to thermosensitive liposomes, non-sensitive liposomes (in this case also referred to as non-thermally sensitive liposomes) do not release their contents due to hyperthermic stimulation, such as at temperatures less than about 15 degrees higher than basal mammalian body temperature, i.e., above about 37° C. The present disclosure encompasses the use of non-sensitive liposomes that are less than about 400 nm in diameter, such as, for example liposomes having a diameter of about 200 nm or about 120 nm in diameter to facilitate handling, administration, unhindered progress through mammalian vasculature, ability to target damaged or malformed vasculature, and minimize side effects, e.g., interference with the mammalian blood clotting cascade.

As used herein, the term "thermosensitive liposome" means a liposome formulated using physiologically compatible constituents, such as dipalmitoylphosphatidyl-choline and dipalmitoylphosphatidyl-glycerol phospholipids, that permits preparation of liposomes using art-recognized techniques that release their contents at temperatures at least about 3 degrees higher than about 37° C. (normal mammalian body temperature). Upon exposure to temperatures at least about 3° C. above basal mammalian body temperature, release of liposome contents occurs by leakage or seepage or by actual lysis (complete or incomplete) of the liposomes. The present disclosure encompasses the use of thermosensitive liposomes that are less than about 400 nm in diameter, such as, for example liposomes having a diameter of about 200 nm or about 120 nm in diameter to facilitate handling, administration, unhindered progress through mammalian vasculature, and minimize side effects, e.g., interference with the mammalian blood clotting cascade.

As used herein, the term "transition elements" means those elements found in columns IIIB, IVB, VB, VIIB, VIIIB IB and IIB of the Periodic Table of Elements. Transition elements are also known as d-block elements.

II. General Considerations

One aspect of the present disclosure involves magnetic resonance-based techniques in general, and magnetic resonance imaging techniques in particular. The magnetic resonance imaging techniques employed herein are known and are described, for example, in Kean & Smith, (1986) *Magnetic Resonance Imaging: Principles and Applications*, Williams and Wilkins, Baltimore, Md. U.S.A. Representative MR techniques include, but are not limited to, magnetic resonance imaging ("MRI"), nuclear magnetic resonance ("NMR") and electronic spin resonance ("ESR").

Standard MR equipment, conditions and techniques can be used to generate images. Appropriate equipment, conditions and techniques can be determined in the course of experimental design. When in vivo MRI experiments are performed in the context disclosed herein, they can be performed on any suitable MRI instrument, such as a 1.5 Tesla or higher whole-body scanner.

According to known principles, nuclei with appropriate spin, when placed in an applied magnetic field ($B_0$, expressed generally in units of Tesla) align in the direction of the field. In the case of protons, these nuclei precess at a frequency, f, of 42.6 MHz, at a field strength of 1 Tesla (T). At this frequency, an RF pulse of radiation will excite the nuclei and can be considered to tip the net magnetization out of the field direction, the extent of this rotation being determined by the pulse energy (which can be obtained by integrating a time×amplitude curve). After the RF pulse, the nuclei "relax" or return to equilibrium with the magnetic field, emitting radiation at the resonant frequency. The decay of the emitted radiation is characterized by two relaxation times, i.e., $T_1$, the spin-lattice relaxation time or longitudinal relaxation time, that is, the time taken by the nuclei to return to equilibrium along the direction of the externally applied magnetic field, and $T_2$, the spin-spin relaxation time associated with the dephasing of the initially coherent precession of individual proton spins. These relaxation times have been established for various fluids, organs and tissues in different species of mammals.

MRI is a diagnostic and research procedure that uses a large, high-strength magnet and radio frequency signals to produce images. The most abundant molecular species in biological tissues is water. It is the quantum mechanical "spin" of the water proton nuclei that ultimately gives rise to the signal in standard imaging experiments. Other nuclei can be employed in MRI applications, however low signal-to-noise (S/N) ratios are a consideration in these applications. In an MRI experiment, the sample to be imaged is placed in a strong static magnetic field (on the order of 1-12 Tesla) and the spins are excited with a pulse of radio frequency ("RF") radiation to produce a net magnetization in the sample. Various magnetic field gradients and other RF pulses then act on the spins to code spatial information into the recorded signals. The basic MRI experiment can be described, in one frame of reference, as follows. Pre-RF pulse spins can be thought of as collectively aligned along the Z-axis of a Cartesian coordinate system; application of one or a sequence of RF pulses "tip" the spins into the X-Y plane, from which position they will spontaneously relax back to the Z-axis. The relaxation of the spins is recorded as a function of time. Using this basic experiment, MRI is able to generate structural information in three dimensions in a relatively short period of time.

By applying magnetic field gradients so that the magnitude of the magnetic field varies with location inside the subject-receiving space characteristics of the magnetic resonance signals from different locations within the region, such as the frequency and phase of the signals, can be made to vary in a predictable manner depending upon position within the region. Thus, the magnetic resonance signals are "spatially encoded" so that it is possible to distinguish between signals from different parts of the region. After repeating this procedure with various different gradients, it is possible to derive a map showing the intensity or other characteristics of the magnetic resonance signals versus position within the excited region. Because these characteristics vary with concentration of different chemical substances and other characteristics of the tissue within the subject's body, different tissues provide different magnetic resonance signal characteristics. When the map of the magnetic resonance signal characteristics is displayed in a visual format, such as on screen or on a printed image, the map forms a visible picture of structures within the patient's body.

Two characteristic relaxation times are implicated in magnetic relaxation, the basis for MRI. $T_1$ is defined as the longitudinal relaxation time, and is also known as the spin lattice relaxation time ($1/T_1$ is a rate constant, $R_1$, the spin-lattice relaxation rate constant). $T_2$ is known as the transverse relaxation time, or spin-spin relaxation mechanism, which is one of several contributions to $T_2$ ($1/T_2$ is also a rate constant, $R_2$, the spin-spin relaxation rate constant). $T_1$ and $T_2$ have inverse and reciprocal effects on image intensity, with image intensity increasing either by shortening the $T_1$ or lengthening the $T_2$.

In another aspect, the presently disclosed subject matter involves the use of the technique commonly referred to as "hyperthermia". Hyperthermia, generally, is a technique for locally heating a site of interest to a temperature above normal body temperature. Hyperthermia is an established technique and forms the basis of several therapeutic regimens. For example, typical localized-hyperthermia temperatures required for therapeutic treatment of cancer are in the 42.5-45° C. range, which is maintained for approximately 30 to 60 minutes. Healthy tissue, generally, should be kept at temperatures below 42.5° C. during the treatment. For targeted chemotherapy drug delivery, temperatures in the range of about 40 to 45° C. have been demonstrated to be effective on tumors.

In another aspect of the presently disclosed subject matter, a composition (e.g., an envirosensitive or non-sensitive liposome composition) can be introduced into a biological structure disposed in a subject. The mode of administration of a composition to a sample or subject can determine the sites and/or cells in the organism to which an agent will be delivered. The compositions can be administered in admixture with a pharmaceutical diluent (e.g., a buffer) selected with regard to the intended route of administration and standard pharmaceutical practice. The compositions can be injected into a subject parenterally, for example, intra-arterially or intravenously. For parenteral administration, a preparation can be used, e.g., in the form of a sterile, aqueous solution; such a solution can contain other solutes, including, but not limited to, salts or glucose in quantities that will make the solution isotonic. In another aspect, a composition can be injected directly into a tumor. In this aspect, the preparation will be injected in accordance with the above guidelines.

When a composition is administered to humans, the supervising physician or clinician will ultimately determine the appropriate dosage for a given human subject, and this can be expected to vary according to the weight, age and response of the individual as well as the nature of the patient's condition.

III. Contrast Agents

Paramagnetic contrast agents serve to modulate tissue (or intrinsic) $T_1$ and/or $T_2$ values, and are typically designed with regard to a given metal nucleus, which is usually selected based on its effect on relaxation. The capacity to differentiate between regions or tissues that can be magnetically similar but histologically different is a major impetus for the preparation of these agents. Paramagnetic contrast agents provide additional image contrast, and thus enhanced images, of those areas where the contrast agent is localized. For example, contrast agents can be injected into the circulatory system and used to visualize vascular structures and abnormalities (see, e.g., U.S. Pat. No. 5,925,987), or even intracranially to visualize structures of the brain.

The measured relaxivity of the contrast agent is dominated by the selection of the metal atom. Paramagnetic metal ions, as a result of their unpaired electrons, act as potent relaxation enhancement agents. They decrease the $T_1$ relaxation times of nearby spins, exhibiting an $r^6$ dependency, where r is the distance between the two nuclei. Some paramagnetic ions decrease the $T_1$ without causing substantial linebroadening, for example copper(II) ("Cu(II)"), zinc(II) ("Zn(II)"), gadolinium(III) ("Gd(III)") and manganese(II) ("Mn(II), while others induce drastic linebroadening, for example, superparamagnetic iron oxide. The mechanism of $T_1$ relaxation is generally a through-space dipole-dipole interaction between the unpaired electrons of a metal atom with an unpaired electron (the paramagnet) and those water molecules not coordinated to the metal atom that are in fast exchange with water molecules in the metal's inner coordination sphere.

When designing or selecting a liposome composition according to the present disclosure, an appropriate paramagnetic ion can be selected as a contrast agent. Any compound that affects the recovery of the magnetic moment of the water protons to the magnetic field, thereby reducing the $T_1$ and $T_2$ relaxation times of an object of interest is suitable for use as a contrast agent with the methods and compounds disclosed herein. Some example metal ions suitable for use include, but are not limited to, the transition, lanthanide and actinide elements. For example, the metal ion is selected from the group consisting of Gd(III), Cu(II), Cr(III), Fe(II), Fe(III), Co(II), Er(II), Ni(II), Eu(III), Dy(III), Zn(II), Mg(II), Mo(III), Mo(VI), Li(I), Ta(V), and Mn(II).

IV. Liposome Compositions

Drug delivery systems have been developed in which a drug-entrapping liposome composition is intravenously administered and delivered to a particular target site in the subject's body (see, e.g., Gregoriadis et al.; (1980) *Receptor-mediated Targeting of Drugs*, Plenum Press, New York, pp. 243-266). A requirement of such systems is that the liposome composition, after being intravenously or intra-arterially administered, should stably circulate along with blood in the subject's body for a longer period of time than provided by conventional systems.

Liposomes are generally not very stable in blood due to interactions between the liposomes' membrane component lipid and blood components such as lipoprotein. Also, intravenously and intra-arterially administered liposomes are sometimes recognized as a foreign substance by the reticuloendothelial system (RES) and are thus likely to be removed from the blood, due to the liposomes' physical morphology and biochemical properties.

Significant efforts have been devoted to solving the problem of stabilizing liposomes in blood to avoid recognition by the RES, and thus, to enhance the liposomes' effective lifetime in the blood. For example, one paper reports a case in which cholesterol was added to liposome membrane composition to increase blood liposome stability (Knight; (1981) *Liposomes: From physical structure to therapeutic applications*, Elsevier, North Holland, pp. 310-311). However, the effect thus obtained varies widely depending on the original membrane composition of the liposome (Senior et al., (1985) *Biochim. Biophys. Acta* 839: 1-8). It has been reported that sialic acid-containing glycolipid, when administered as liposome, is distributed to the liver, a component of the RES (Surolia & Bachhawat, (1977) *Biochim. Biophys. Acta* 497: 760-765). It has also been reported that a drug was delivered into the brain after increasing the liposome's ability to pass through the blood brain barrier by functionalizing it with sulfatide, a glycolipid and a sulfo group (Naoi & Yagi, (1984) *Biochem. Int.* 9: 267-272).

Recently, thermosensitive liposomes—liposomes that are stable at mammalian body temperature but become less stable at temperatures higher than mammalian body temperature—have been employed to encapsulate chemotherapy agents and to release these agents into heated tissue (see, e.g., U.S. Pat. No. 6,200,598 to Needham et al., incorporated in its entirety herein by reference). For example, successful targeted chemotherapy delivery to brain tumors in animals using thermosensitive liposomes has been demonstrated (Kakinuma et al., (1996) *Int. J. Hyperther.* 12(1): 157-165). The results of this study indicated that when thermosensitive liposomes are employed as a drug carrier, significant chemotherapy drug levels were measured within brain tumors that were heated to the range of about 41 to 44° C. One formulation for a thermosensitive liposome is described in U.S. Pat. No. 5,094,854, incorporated in its entirety herein by reference.

In one aspect, the presently disclosed methods and compositions comprise envirosensitive or non-sensitive liposomes, e.g. thermosensitive and non-thermally sensitive liposome compositions. These liposomes can comprise virtually any particular combination of lipids, and can further comprise proteins, carbohydrates and other types of compounds as well. Some representative, but non-limiting liposome compositions are presented in the following sections and in the Laboratory Examples. Methods of forming the liposomes are also described herein. Generally, the same procedure can be employed for forming both envirosensitive and non-sensitive liposomes (e.g. thermosensitive and non-thermally sensitive liposomes), with one difference being the lipid composition of the liposome.

IV.A. Preparing Non-Sensitive and Envirosensitive Liposomes

Envirosensitive or non-sensitive liposomes can be prepared utilizing techniques such as those employed in the art for conventional liposome preparation. Such conventional techniques are referred to, for example, in Published PCT International Application Serial No. WO 92/21017 and by Papahadjopolous (Papahadiopolous, (1979) *Ann. Rep. Med. Chem.* 14: 250-260) and include reverse evaporation, freeze-thaw, detergent dialysis, homogenization, sonication, microemulsification and spontaneous formation upon hydration of a dry lipid film. In one embodiment, a film of the lipid is deposited on a glass coverslip and then incubated in a sucrose solution for a predetermined time, such as 12 hours. A thin film of lipid is then deposited on the inside of a round bottom flask and then rehydrated at a temperature above its phase transition temperature ($T_m$). Then, the hydrated lipids are sonicated in order to form liposomes.

Thermosensitive liposomes can be formed from a combination of lipids. Although almost any combination of lipids can be employed so long as the desired functional characteristic(s) is/are obtained, in one example, a. thermosensitive liposome comprises dipalmitoylphosphatidylcholine-polyethylene glycol (DPPC-PEG$_{2000}$). In another example, a thermosensitive liposome comprises dipalmitoylphosphatidylcholine-distearoylphosphatidylethanolamine-polyethylene glycol (DPPC-DSPE-PEG$_{2000}$) (95:5, mol:mol), and in yet another example, a thermosensitive liposome comprises polyenylphosphatidylcholine-MSPC-distearoylphosphatidylethanolamine-polyethylene glycol (DPPC-MSPC-DSPE-PEG$_{2000}$) (90:10:4, mol:mol).

Other embodiments of envirosensitive liposomes include, but are not limited to radiation-sensitive liposomes. The radiation-sensitive liposomes disclosed herein can be formed from a combination of lipids. Although almost any combination of lipids can be employed so long as the desired functional characteristic(s) is/are obtained, in one example, a radiation-sensitive liposome comprises dipalmitoylphosphatidylcholine (DPPC), distearoylphosphatidylcholine (DSPC), or diarachidoylphosphatidylcholine-polyethylene glycol (DAPC) in combination with PEG. In another example, cholesterol is added to one or more of these formulations. The addition of cholesterol reduces membrane fluidity and increases membrane integrity.

The radiation-sensitive formulations can further incorporate a radiation-sensitive lipid, which is selected based on the desired wavelength sensitivity. Thus, in one embodiment, liposomes can be made radiation-sensitive by the incorporation into the liposome wall radiation-sensitive lipids that undergo substantial alterations, such as isomerization, fragmentation or polymerization, upon interation with a particular wavelength range of electromagnetic radiation. For example, incorporation of polymerizable lipids such as 1,2-bis[10-(2',4'-hexadienoyloxy)decanoyl]-sn-glycero-3-phosphocholine (bis-SorbPC), react directly with ultraviolet radiation in the presence of oxygen to form cross-linked polymer networks that significantly alter bilayer properties in the liposome wall, resulting in destabilization of the liposome and release of its contents (Bondurant et al., (2001) *Biochimica et Biophysica Acta* 1511: 113-122). Spratt et al. have further shown that using a specific bis-SorbPC (bis-SorbPC$_{19,19}$) will increase reactivity to ultraviolet radiation by a magnitude of at least two orders (Spratt et al., (2003) *Biochimica et Biophysica Acta* 1611: 35-43.

Sensitivity to other wavelength ranges of electromagnetic radiation can be achieved by incorporation of any of a variety of other sensitive lipids or even other non-lipid radiation-sensitive molecules. For example, visible light-sensitive liposomes can be formulated by incorporating dyes into the liposome walls. In one embodiment, ballasted cyanine dyes, such as distearoyl indocarbocyanine, in combination with polymerizable lipids, such as bis-SorbPC, are incorporated into liposome walls to produce light-sensitive liposomes that release their contents when contacted with visible light (green wavelength) (Mueller et al., (2000) *Macromolecules* 33: 4799-4804).

For in vivo biological applications, it can be desirable to use radiation at wavelengths less absorbable by biomolecules than visible or ultraviolet light. Therefore, liposomes incorporating molecules providing radiation-sensitivity at other wavelengths, such as ionizing radiation (e.g. x-rays), or long wavelength radiation (e.g. near-infrared or infrared) can also be formulated similarly to the previously described radiation-sensitive liposomes. One of skill in the art would thus appreciate that radiation-sensitive liposomes providing sensitivity across the electromagnetic spectrum are encompassed by the methods and compositions described herein.

Also included in the methods and compositions described herein are pH-sensitive liposomes. As discussed for thermosensitive liposomes, almost any combination of lipids can be employed so long as the desired characteristics of pH-sensitivity at a particular pH range are obtained. Numerous pH-sensitive liposomes are known and described in the art (see e.g. Litzinger & Huang, (1992) *Biochim Biophys Acta* 1113: 201-227). In one example, dipalmitoyl phosphatidyl ethanolamine/palmitic acid provides a useful pH-sensitive liposome formulation (Lokling et al., (2001) *Magnetic Resonance Imaging* 19: 731-738 and Lokling et al., (2003) *Magnetic Resonance Imaging* 21:531-540). Other formulations having similar properties are also encompassed by the present disclosure. Representative lipid compositions of non-sensitive liposomes include the thermosensitive liposome formulations disclosed herein, with the exception that the non-sensitive formulations often include cholesterol in varying amounts. For example, a non-sensitive liposome can comprise dipalmitoylphosphatidylcholine/cholesterol (DSPC/Cholesterol) (55:45, mol:mol).

Envirosensitive as well as non-sensitive liposomes can be prepared by extrusion methods. Lipids, at certain ratios, such as those described above, can be dissolved in a chloroform-methanol mixture. The solvent can then be removed under a gentle stream of nitrogen gas and the lipid samples subsequently placed under a high vacuum for a time period of at least 4 hours to remove any residual solvent.

The dried samples can then be hydrated such that the final lipid concentration is, for example, about 100 mg/mL. In one embodiment, hydration can be achieved by contacting the dried samples with 300 mM MnSO$_4$ (a contrast agent) adjusted to pH 3.5 by addition of hydrochloric acid. Hydration of the lipid can be performed at a suitable temperature for a desired period of time, for example 55° C. for approximately 30 minutes, and generates multilamellar vesicles (MLVs).

Following hydration, MLVs can be extruded 10-times through stacked polycarbonate filters of 0.1 and 0.08 μm pore size at 55° C. using a water-jacketed extrusion apparatus, such as an EXTRUDER™ apparatus (Northern Lipids Inc., Vancouver, British Columbia, Canada). Extrusion of the MLVs results in liposomes that are ready for loading.

Following preparation, the mean size distribution of a liposome preparation can be determined. For some preparation, a NICOMP Submicron Particle Sizer Model 270 (Pacific Scientific, Santa Barbara, Calif., United States of America) operating at 632.8 nm can be employed, although other methods and apparatuses can also be employed. Phospholipid can also be quantitated, for example by employing a known assay such as the Fiske and Subbarow phosphate assay (Fiske & Subbarow, (1925) *J. Biol. Chem.* 2: 375-395)

Once an envirosensitive or non-sensitive liposome is prepared, the liposome can be loaded with a contrast agent and/or a compound of interest, such as a drug.

Envirosensitive and non-sensitive liposomes can be loaded with a contrast agent and/or a compound of interest by employing any of a range of techniques known in the art. Various methods include osmotic loading, pH gradient-based loading and ionic gradient-based loading (Kulkarni et al., (1995) *J. Microencapsul.* 12(3): 229-46).

In one embodiment, for example, liposome loading can be achieved by fractionating a liposome preparation on a SEPHADEX® G-50 (Amersham Biosciences, Piscataway, N.J., United States of America) column. For the fractionation, 1 mL sample volumes can be placed on a column with at least a 20 mL column bed that has been equilibrated with 500 mM sucrose/20 mM HEPES (N-[2-hydroxyethyl] piperazine-N'-[2-ethanesulfonic acid]) buffer at pH 7.5.

Following fractionation, contrast agent and/or a compound of interest can be loaded by generally following the method described by Abraham et al.

(Abraham et al., (2002) *Biochim. Biophys. Acta* 1565: 59-72).

Alternatively, in another embodiment, liposomes can be loaded using a pH gradient-based technique, such as described by Mayer et al. (Mayer et al., (1985) *J. Biol. Chem.* 260(2): 802-808). Generally, MLVs are produced by extrusion in the presence of $K^+$ and then placed in a $Na^+$ buffer to create a transmembrane $Na^+/K^+$ gradient with $K^+$ concentrated within the vesicle and $Na^+$ outside the vesicle. A contrast agent and/or a compound of interest in the buffer solution is accumulated at high concentrations within the liposome as a result of the transmembrane gradient. The rate of uptake of the contrast agent and/or compound of interest can be increased by the presence of an ionophore, such as, for example, valinomycin. Uptake is also sensitive to pH with this system, and can be maximized based on the pK of the contrast agent and/or compound of interest.

By way of example, loaded thermosensitive liposomes can be stored at 4° C. for 3-4 days. Loaded non-sensitive liposomes can be stored for about 1-3 weeks at 4° C. Envirosensitive and non-sensitive liposomes that have not been loaded can be stored for about 3-4 weeks at 4° C. Unloaded envirosensitive and non-sensitive liposomes can also be lyophilized and stored in that form.

This approach can be employed in the preparation of envirosensitive and non-sensitive liposomes. After liposomes are loaded, they can be stored in a suitable buffer solution and will be immediately ready for use without further preparation.

V. Applications

The presently disclosed methods and compositions can be employed in a variety of applications. Several of these applications are described in detail hereinbelow. Additional applications of the presently disclosed methods and compositions will be apparent to those of ordinary skill in the art upon consideration of the present disclosure.

In the following applications, standard magnetic resonance imaging apparatus and methodology can be employed, as would be apparent to those of ordinary skill in the art after a review of the present disclosure.

V.A. Monitoring the Accumulation of a Compound of Interest at a Desired Site In Vivo In one application, a method of monitoring the accumulation of a compound of interest at a desired site in vivo by magnetic resonance imaging is disclosed. This application can be useful for tracking the delivery of a compound of interest to a site of interest, for example a tumor and for assuring that the compound of interest is delivered to the site in useful quantities.

In one embodiment, the method comprises increasing blood flow to a site of interest. As noted herein, a site of interest can be a tumor. In other examples, a site of interest can comprise a biological organ, such as the brain, liver, kidney or eye. In yet other examples, a site of interest can comprise a specific region or structure associated with the vasculature of a subject, or can even comprise the subject's vascular system in its entirety.

After selecting a site of interest, blood flow is increased to the site of interest. Heating can be used as an effective approach for increasing the blood flow to the site of interest. The heat results in vasodilation at the desired site and a subsequent increase in blood flow to the site. Heating can be achieved by employing any of a variety of techniques. For example, a site can be heated by RF energy, via application of ultrasonic energy or by conduction-based heating methods. When conduction-based heating methods are employed, one convenient method of heating is by contacting the site of interest with a catheter that is heated to a desired temperature, for example, with circulating water. When a site of interest is near an exposed surface of the subject (e.g., skin or eye), a laser can also be employed to heat the site.

A subject is then administered a non-sensitive liposome composition comprising (i) a contrast agent; (ii) a compound of interest; and (iii) a non-sensitive liposome encapsulating the contrast agent and the compound of interest.

Administration can be by an approach adapted to introduce the non-sensitive liposome composition into the bloodstream of the subject. For example, the administration can be by injection into an artery or vein. In one particular example, when a subject is a rat (for example, a Fisher 344 female strain rat), a liposome composition can be injected into the tail vein or femoral vein of the rat. Thus, administration can be, for example, via intravenous, intramuscular, intraperitoneal, intra-tumoral or subcutaneous intra-lesional injection.

A contrast agent can comprise any paramagnetic nucleus containing material, as disclosed herein above. Compounds comprising transition, lanthanide and actinide elements can also be employed. For example, a contrast agent can comprise an atom of an inner block element, e.g. a manganese atom. A contrast agent can also comprise a chemical moiety associated with the atom, such as a sulfate moiety, in which case a contrast agent can comprise $MnSO_4$, which exhibits a linear relationship between concentration and $1/T_1$ (see FIG. 1B) and $1/T_2$.

A compound of interest can comprise any compound. For example, a compound of interest can comprise a pharmaceutically active compound, such as a chemotherapeutic compound (e.g. methotrexate, doxorubicin, cisplatinum, carboplatinum). A compound of interest can also comprise a compound suspected of being pharmaceutically active. In other cases, a compound of interest can generally comprise a compound known or suspected of modulating one or more biological processes. For example, a compound of interest can be a polypeptide or a polynucleotide. A non-sensitive liposome composition also comprises a non-sensitive liposome encapsulating the contrast agent and the compound of interest. Compositions of non-sensitive liposomes are disclosed herein, as are methods for preparing and loading the liposomes.

Continuing with the present embodiment, the accumulation of the compound of interest at the site of interest is monitored by magnetic resonance imaging. As the non-sensitive liposomes that have been administered to the subject circulate in the bloodstream of the subject, they will tend to accumulate at the site of heating. Over a given time interval, the presence of the liposomes at the heated site will increase. Thus, as time progresses, the presence of contrast agent at the heated site will concomitantly increase (see FIG. 2A), since the contrast agent is encapsulated in the non-sensitive liposomes.

Figure 2A:
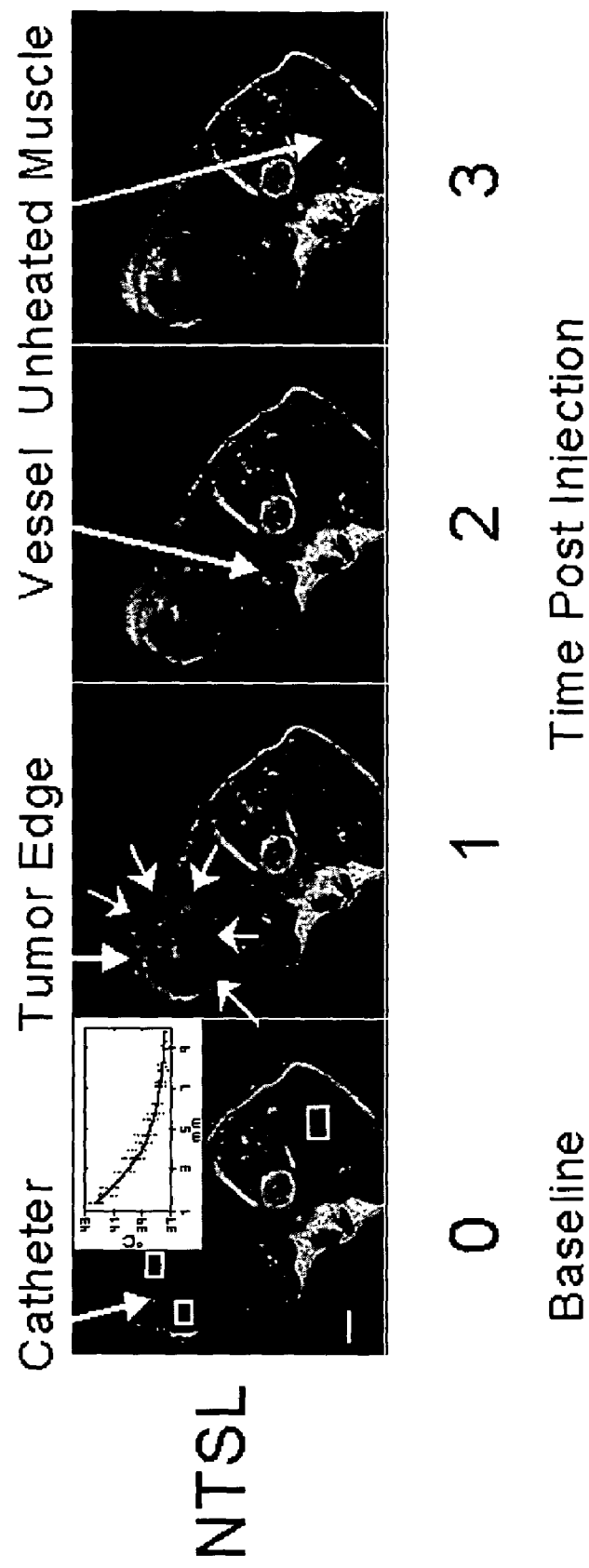
FIG. 2A is a time course of MR images depicting the accumulation of non-sensitive liposomes at a flank tumor in a rat. Panel 0 corresponds to time T=0 minutes (pre-injection); panel 1 corresponds to time T=5 minutes; panel 2 corresponds to time T=30 minutes; and panel 3 corresponds to time T=90 minutes.

Magnetic resonance images of the heated site can be continuously and regularly generated, as depicted in FIG. 2A. Methods of acquiring magnetic resonance images are established and can be employed to generate magnetic resonance images of a heated site. A sequence of images of the heated site shows the accumulation of the contrast agent at the heated site and in the areas surrounding the heated site (see FIG. 2A). Since the contrast agent and the compound of interest are both encapsulated in the non-sensitive liposome, the accumulation of the contrast agent is directly proportional to the accumulation of the compound of interest.

As depicted in FIG. 2A, accumulation of the contrast agent at a heated site is evidenced by an increase in the appearance of white pixels in a timecourse series of images. For example, in FIG. 2A at time point 0, immediately after injection of a non-sensitive liposome composition, in particular, a thermoinsensitve liposome composition, there is no contrast agent found at the site of the tumor, which is heated by hot water flowing through a catheter, shown as a black spot in the image. At time point 1, contrast agent, and thus the compound of interest, which is encapsulated with the contrast agent, is accumulating at the periphery of the tumor. This is evidenced by the appearance of white pixelation at the tumor edge. At time point 2, the concentration of contrast agent and compound of interest is increased. At time point 3, the intensity of pixelation is seen to slightly increase over the concentration at time point 2. By way of comparison, no contrast agent or compound of interest is seen to appear in areas that are not heated.

It is noted that as the non-sensitive liposome compositions accumulate at the heated site, they remain structurally coherent and the contents of the liposomes, namely a contrast agent and a compound of interest, remain inside the liposome. Thus, the accumulation of the compound of interest at a heated site can be monitored.

As FIG. 2A demonstrates, this technique can be performed in vivo, with the liposomes eventually being cleared by the renal and/or hepatic systems of the organism. It is possible to perform the method in vitro, on a tissue culture, for example, but most commonly the method will be performed in vivo on a subject.

V.B. In Vivo Method of Monitoring the Localization and Distribution of a Compound of Interest to a Desired Site in a Subject Difficulties in delivering drugs to solid tumors in the human body have been documented in the art. For example, abnormal vessels in tumors can restrict local blood flow in tumors and, hence, impede the delivery of drugs to the tumor. Abnormally elevated interstitial pressure within the tumor is also known to retard the passage of drug molecules from the blood stream into the tumor (Baxter & Jain, (1989) *Microvasc. Res.* 37(1): 77-104; Baxter & Jain, (1990) *Microvasc. Res.* 40(2): 246-63; Baxter & Jain, (1991) *Microvasc. Res.* 41(1): 5-23; Baxter & Jain, (1991). *Microvasc. Res.* 41(2): 252-72)

Effective cancer chemotherapy depends on delivery of therapeutic drugs to cancer cells at cytotoxic concentrations. Due to the inherent perfusion limitations that tumors present, delivery of drugs can be hindered. The ability to monitor and/or predict in vivo concentration distributions could improve treatment. Thus, in one aspect of the present disclosure, envirosensitive liposomes can be employed for in vivo monitoring of drug release and distribution from an envirosensitive liposome using MRI. In vitro results disclosed herein (FIG. 1B) indicate that $T_1$ or $T_2$ shortening correlates with contrast agent (e.g., $MnSO_4$) concentration. Further, contrast agent release from envirosensitive liposomes, for example thermosensitive liposomes, significantly shortens $T_1$ and $T_2$ and thus can be used to monitor content release.

Figure 2B:
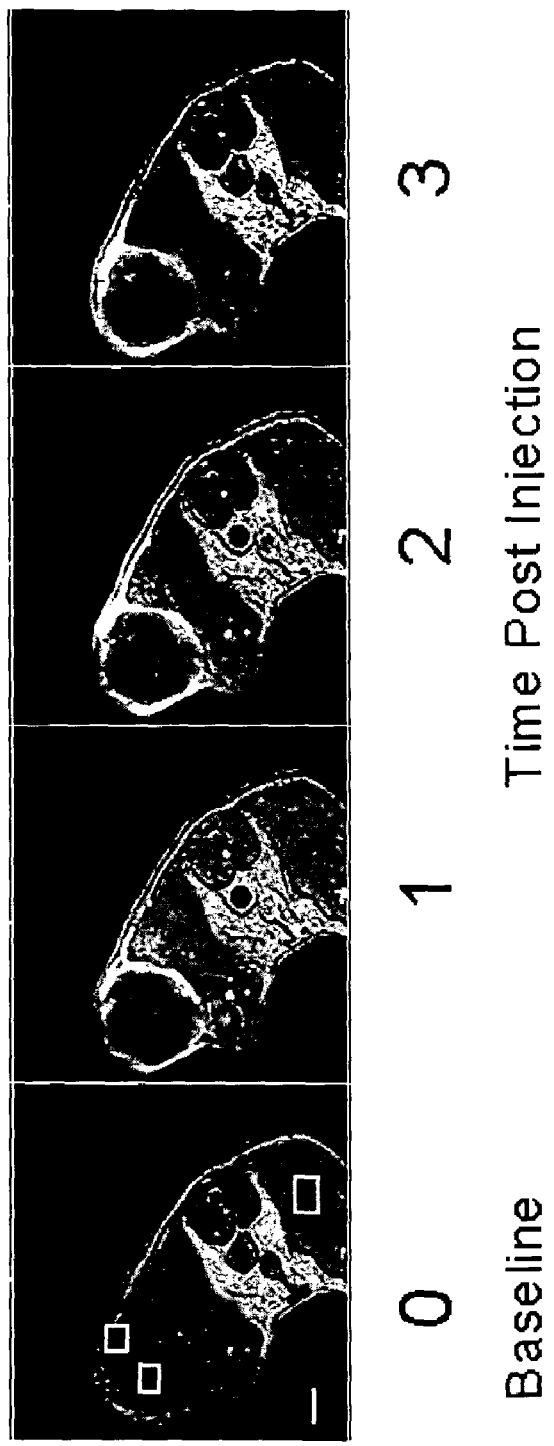
FIG. 2B is a time course of MR images depicting the accumulation of thermosensitive liposomes at a flank tumor in a rat. Panel 0 corresponds to time T=0 minutes (pre-injection); panel 1 corresponds to time T=5 minutes; panel 2 corresponds to time T=30 minutes; and panel 3 corresponds to time T=90 minutes.
Figure 2C:
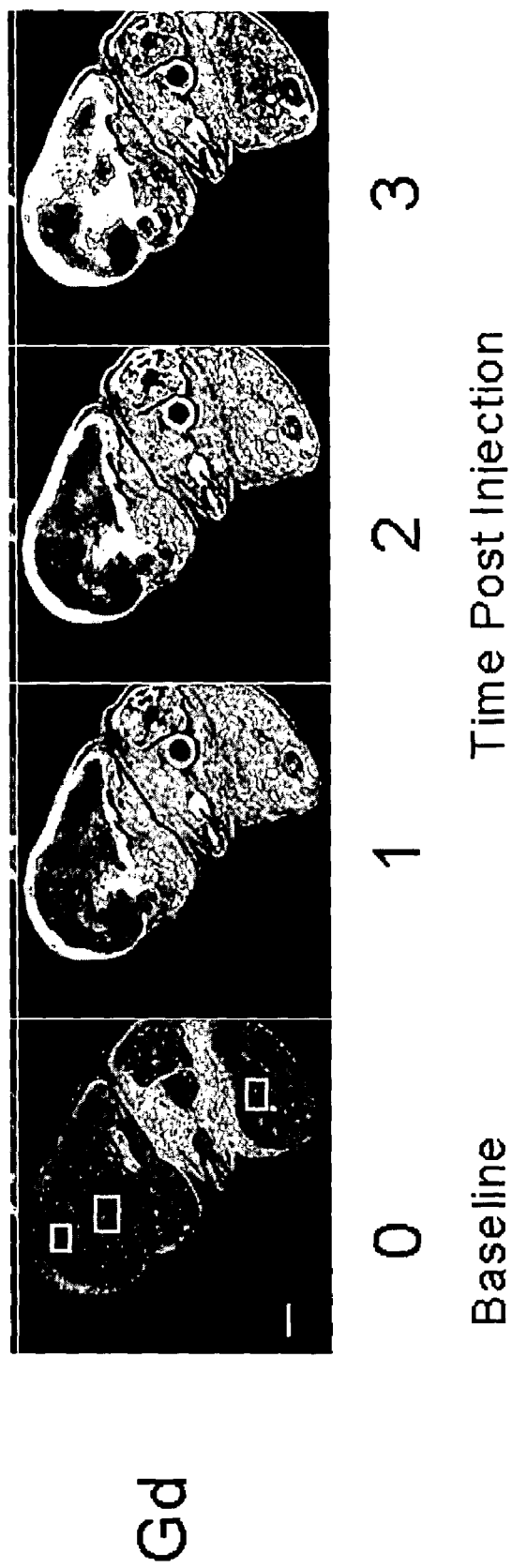
FIG. 2C is a time course of MR images depicting the accumulation of gadolinium-DTPA at a flank tumor in a rat. Panel 0 corresponds to time T=0 minutes (pre-injection); panel 1 corresponds to time T=1 minutes; panel 2 corresponds to time T=5 minutes; and panel 3 corresponds to time T=15 minutes.
Figure 2D:
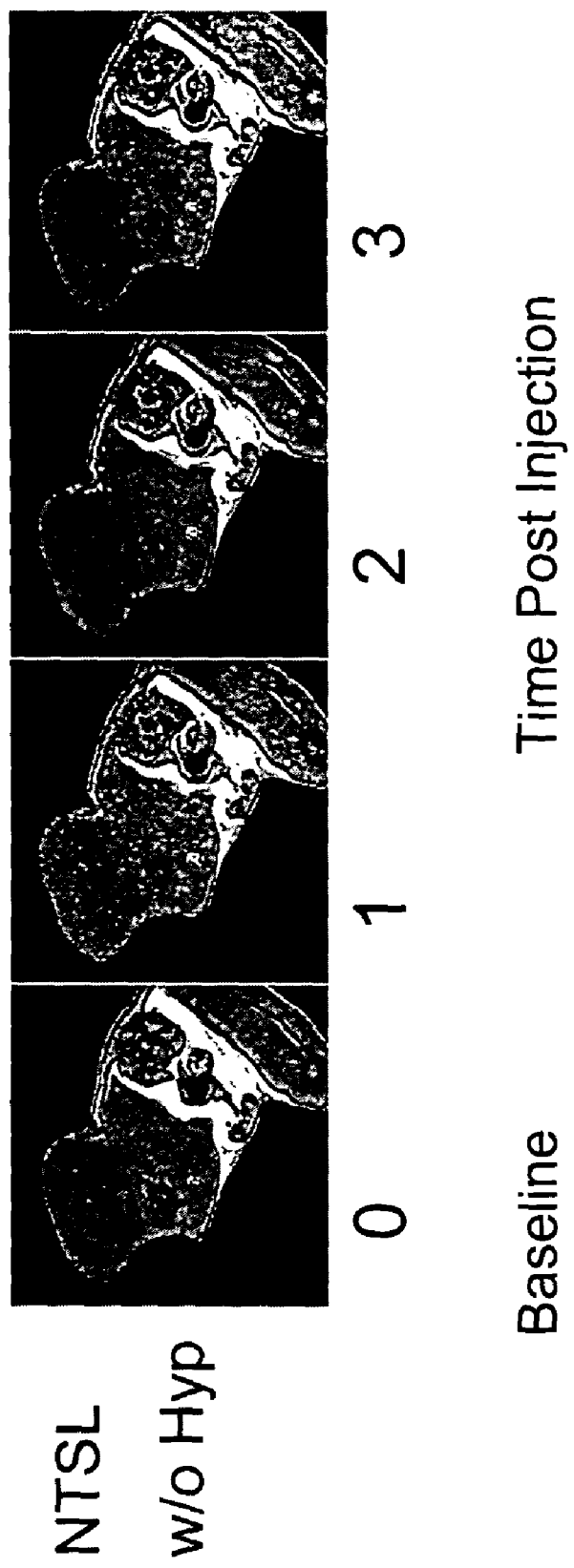
FIG. 2D is a time course of MR images depicting the accumulation of non-sensitive liposomes at a flank tumor in a rat without hyperthermia treatment. Panel 0 corresponds to time T=0 minutes (pre-injection); panel 1 corresponds to time T=5 minutes; panel 2 corresponds to time T=30 minutes; and panel 3 corresponds to time T=90 minutes.
Figure 2E:
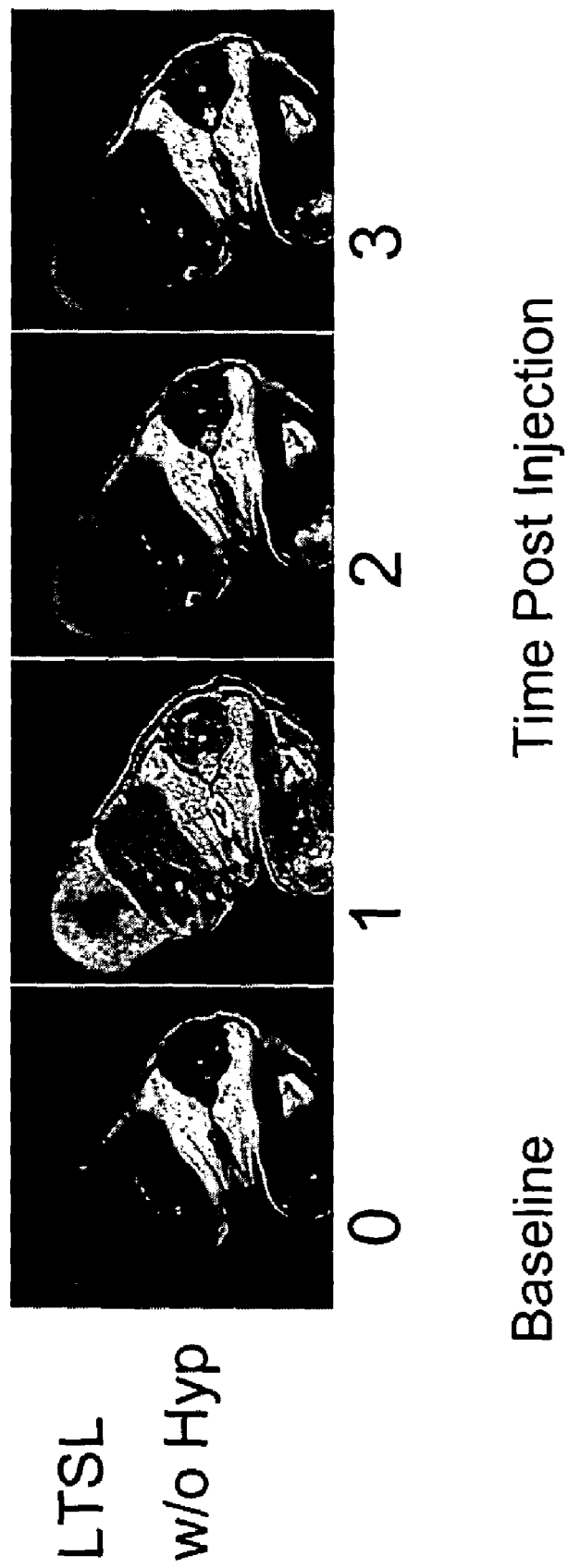
FIG. 2E is a time course of MR images depicting the accumulation of thermosensitive liposomes at a flank tumor in a rat without hyperthermia treatment. Panel 0 corresponds to time T=0 minutes (pre-injection); panel 1 corresponds to time T=5 minutes; panel 2 corresponds to time T=30 minutes; and panel 3 corresponds to time T=90 minutes.

The feasibility of using this drug delivery-imaging agent in vivo was shown in a murine tumor model (FIGS. 2A-2E). These experiments demonstrate that upon tumor heating, thermosensitive and non-sensitive liposomes selectively collect at the site of the tumor, and that thermosensitive liposomes release their contents. In addition, FIG. 2E shows that without heating, a less intense but more uniform signal enhancement occurs, but then fades after five minutes as clearance from the vasculature occurs. However, there is enhancement remaining in the tumor (compared to baseline) indicating that some of the liposomes have collected at the site. The thermosensitive and non-sensitive compositions and methods of the present disclosure, facilitate clinical treatment by providing individualized monitoring of tissue drug concentration distribution. Individualized monitoring provides at least (1) the ability to modify treatment variables to improve the uniformity of drug delivery; and (2) the ability to select patients most likely to benefit from a liposomal treatment as disclosed herein.

Additionally, the methods of loading envirosensitive and non-sensitive liposomes disclosed herein are applicable to a wider spectrum of compounds of interest (e.g., drugs) than was previously possible with pH loading methods, thereby broadening its applicability to other formulations.

In accordance with the present disclosure, an in vivo method of monitoring the distribution of a compound of interest to a desired site in an organism by magnetic resonance imaging is disclosed. In one embodiment, the method comprises increasing blood flow to a site of interest in a subject by, for example, applying heat. The site can be heated by external application of hot water, RF, ultrasound, or IR energy. Alternatively, interstitial application of energy can be obtained using the same physical methods. The heat results in vasodilation at the desired site and an increase in blood flow to the site. Other methods of increasing vasodilatation and blood flow to the site are also acceptable for targeting the liposomes to a desired site. For example, direct mechanical massage or ultrasound treatment to the site can increase blood flow without the use of heat.

As described herein, a subject can be any living organism, for example, a human, mouse, rat, or rabbit, or a subject can be derived from a living organism and can comprise, for example, a tissue culture. A site of interest can comprise any biological structure. For example, a site of interest can comprise a tumor or an organ, such as a brain, liver, kidney, stomach, eye or lung.

Continuing with this embodiment, a thermosensitive liposome composition can be administered to the subject. Again, the administration can be by convenient method, such as injection of the composition into a vein or artery of the subject.

An envirosensitive liposome composition of the present disclosure comprises a contrast agent; a compound of interest; and an envirosensitive liposome encapsulating the contrast agent and the compound of interest. The contrast agent can comprise any paramagnetic material, for example $MnSO_4$ or any compound comprising, for example, a transition element or an inner block element. A contrast agent can comprise a paramagnetic material complexed with an organic material (e.g., a chelator) or an inorganic material (e.g., a sulfate moiety).

A compound of interest can comprise any compound. Such a compound can comprise a chemotherapeutic agent, pharmaceutically active agent or an agent suspect to be of therapeutic value to the subject. Doxorubicin is employed as a non-limiting embodiment of such a compound in the Laboratory Examples.

Additionally, one embodiment of the method comprises monitoring the localization and distribution of the compound of interest to the desired site by magnetic resonance imaging. The embodiment permits monitoring of both localization to the site of interest and distribution of the compound of interest to the site using magnetic resonance imaging. Distribution of the compound of interest refers to release of the compound from the liposome and dispersion of the compound at the site. The monitoring can be conveniently achieved by acquiring magnetic resonance images at any desired time point. Standard magnetic resonance techniques can be employed to generate such images.

In one embodiment, envirosensitive liposomes in the form of thermosensitive liposomes are used. The thermosensitive liposomes are stable at temperatures near mammalian body temperature, about 37° C. The temperature of the heated site will be several degrees above 37° C. As the thermosensitive liposomes travel to the heated site (e.g., through the circulatory system of the subject), they will accumulate at the heated site due, in part, to their size and release their contents due to their thermoinstability.

After exposure to heat for a period of time, the thermosensitive liposomes will become "leaky". That is, the thermosensitive liposomes will lose a degree of structural integrity, allowing the contents of the liposomes, namely a contrast agent and a compound of interest, to be released from the thermosensitive liposome. The release of the contents of the thermosensitive liposome can be tracked by monitoring an increase in the presence of contrast agent at a range of points around a given structure. The association of contrast agent with a structure is denoted by an increase in the pixelation around the structure in a MR-generated image.

Turning now to FIG. 2B, application of one embodiment of the method is depicted in a series of MR images. The images correspond to the effect of injecting loaded thermosensitive liposomes into the tail vein of a rat. The images generally depict association of contrast agent with the periphery of a large flank tumor.

At time point 0, a thermosensitive liposome composition has been injected into the circulatory system of the rat. The flank tumor is heated by inserting a catheter heated with circulating water and appears as a black spot in the upper left of the image.

At time point 1 (corresponding to about 15 minutes), the loaded thermosensitive liposomes have accumulated at the heated site and have released their contents. The association of the contrast agent with the periphery of the tumor is evidenced by the pixelation (which appears white in the figure) surrounding the tumor mass.

At time point 2 (corresponding to about 30 minutes), the pixelation is seen to be more intense, indicating the further release of contrast agent from the thermosensitive liposomes. The periphery of the tumor is even more completely surrounded by contrast agent.

At time point 3 (corresponding to about 90 minutes), the pixelation is less intense, indicating that the contrast agent is being cleared and the concentration in the vicinity of the tumor is decreasing.

In addition, FIG. 2E shows that without heating, a less intense but more uniform signal enhancement occurs, but then fades after five minutes as clearance from the vasculature occurs.

In a similar embodiment, envirosensitive liposomes in the form of radiation-sensitive liposomes are used. Like other envirosensitive liposomes, including the previously described thermosensitive liposomes, radiation-sensitive liposomes are stable under normal physiological conditions.

The radiation-sensitive liposomes also travel to and accumulate at the heated site due, in part, to their size. However, unlike thermosensitive liposomes, the radiation-sensitive liposomes will not be expected to release their contents when heated, unless the heat source is producing a wavelength of electromagnetic radiation within the range of sensitivity of the particular radiation-sensitive liposomes.

Instead, a source of electromagnetic radiation emitting radiation at a wavelength within the range of sensitivity of the particular radiation-sensitive liposomes is directed at the site, which then interacts with susceptible lipids in the liposome wall. The sensitive lipids then either isomerize, fragment or polymerize, which then causes the liposomes to lose structural integrity and increase permeability, in some formulations, sufficiently to release their contents. Namely, the radiation-sensitive liposomes become permeable enough to at least allow exchange of water across the membrane. The membrane in some formulations will become sufficiently permeable to release the contained contrast agent and/or compound of interest. As already described, the release of contents can be tracked by monitoring the presence of contrast agent at a range of points around a given structure.

One of skill in the art will appreciate that other liposome disruption agents can be used, such as pH variance, depending on the disruption characteristics of the particular envirosensitive liposome formulated.

In another aspect, drug release can also be quantified. One method of quantifying drug release generally involves employing a plot of concentration against $1/T_1$ or $1/T_2$ as a calibration curve.

Continuing with this embodiment, before a given experiment is performed, the $T_1$ of a pixel is measured. This $T_1$ measurement can provide additional information, including proton density and base line noise. If all the imaging parameters (e.g., $T_r$, PD, etc.) are kept constant, which is typical in a dynamic study, a change in signal intensity at a time point later than time t=0 is accompanied by a reduction in $T_1$. Such a change in $T_1$ is indicative of localization and distribution of a drug from an envirosensitive liposome composition. This reduction in $T_1$ can be converted to concentration using the plot of concentration against $1/T_1$ as a standard curve for the corresponding compound. Thus, observed changes in $T_1$, which are associated with drug release, can be translated into a released drug concentration by indexing the observed $T_1$ with a given concentration on a plot of concentration against $1/T_1$.

V.C. Method of Detecting an In Vivo Blood Pool

Contrast agents with prolonged presence in the blood (i.e., good resistance to uptake by RES and a relatively low diffusivity into the tissue or extravascular locations) are recognized in the art as useful "blood pool agents" (see, e.g., U.S. Pat. No. 5,464,696, herein incorporated by reference in its entirety). Contrast agents exhibiting long biological half-lives are sometimes desirable for the blood pool agents if a researcher or clinician desires to produce meaningful analytical results and to eliminate repeated injections and the repeated use of a contrast agent.

Several attempts to produce compositions suitable for use as blood pool agents have been made, including some for use with MRI (see, e.g., U.S. Pat. Nos. 5,833,948; 5,464,696; 6,010,681; 5,961,953; and 5,888,476, herein incorporated by reference in its/their entirety). Particularly, there has been an ongoing effort to develop contrast agents with long residence times in the blood circulation, that exhibit high relaxivity and can be completely eliminated from the system of a subject (i.e., agents that can be employed as "blood pool agents"). Some efforts have focused on identifying and preparing paramagnetic substances encapsulated into liposome vesicles, immobilized in the liposome membrane, copolymerized with polyethylene glycol or grafted on a polymeric chain such as albumin, dextran or polylysine. Examples of such compositions include Gd-DTPA-albumin, Gd-DTPA-dextran or Gd-DTPA-polylysine complex molecules (see, e.g., Ogan et al., (1987) *Invest. Radiol.* 22: 665; Wang et al., (1990) *Radiology* 175: 483; Schumann-Giampieri et al., (1991) *Invest. Radiol.* 26: 969; Vexler et al., (1994) *Invest. Radiol.* 29 supl. 2: S62; Dessler et al., (1994) *Invest. Radiol.* 29 supl. 2: S65; Meyer et al., (1994) *Invest. Radiol.* 29 supl. 2: S90; Shen et al., (1994) *Invest. Radiol.* 29 supl. 2: S217).

Notwithstanding, the half-life of contrast agents containing paramagnetic species bonded to macromolecules is often too short to be convenient for blood-pool imaging or have unexpected toxic side effects. In order to solve this difficulty, the use of suspensions of liposomal microvesicles containing encapsulated paramagnetic chelates as carriers of NMR contrast agents has been proposed. Use of liposomes for carriers has been proposed for relative biocompatibility and ease of preparation of liposomes and their suspensions. Encapsulation of known paramagnetic contrast agents into liposomes has been described (see, e.g., Unger et al., (1993) *J. Mag. Res. Imag.* 3: 195-198).

These known compositions exhibit longer dwelling times in the blood than the water-soluble metal complexes; however, their residence times in the circulation are still not sufficient and some of these compounds have shown unacceptable levels of toxicity for blood-pool imaging. Longer residence times and lower immunogenicity have been reported by Bogdanov et al. (Bogdanov et al., (1993) *Radiology* 187: 701) for Gd-DTPA-MPEG-polylysine complexes which consist of a methoxy(polyethylene glycol)-shielded macromolecular backbone (polylysine) bearing covalently attached Gd-DTPA. However, these prior art compositions do not offer the advantages of the compositions and methods disclosed herein.

Desirable properties of a blood pool agent include the ability to remain in a subject's bloodstream for protracted periods of time. For contrast agents administered into the systemic vasculature, as a general rule, low molecular weight hydrophilic molecules (e.g. molecular weight beneath about 5000 Da) distribute into the extracellular fluid (ECF) and are relatively rapidly excreted through the kidneys by glomerular filtration. Particulates, liposomes or lipophilic molecules tend to accumulate relatively rapidly in the liver. Thus, an effective blood pool agent would not be recognized by the RES, and would remaining in the bloodstream for an extended period, yet would still provide a magnetic relaxation response. The blood pool agents disclosed herein accomplish this goal.

The use of a blood pool agent can facilitate a wide range of measurements that can be of interest to researchers and clinicians. For example, one role that a blood pool agent can play is as an aid in the measurement of blood volumes and the blood perfusion of various organs, including the brain, using in vivo, non-invasive techniques.

Accordingly, in one aspect of the present disclosure, a method of detecting an in vivo blood pool is disclosed. In one embodiment of the method, a subject is administered a non-sensitive liposome composition. A suitable non-sensitive liposome composition can comprise a contrast agent and a non-sensitive liposome encapsulating the contrast agent. The administering can be carried out by any convenient method, although many times injection of the composition into a subject's vein or artery can be the most convenient approach to administering a composition.

A subject, as described herein, can be any living organism or a subject can even comprise a solution (e.g. blood, plasma, etc.) infused tissue culture. A contrast agent can comprise any paramagnetic material, such as $MgSO_4$. Many such materials are commercially available and can be employed in a non-sensitive liposome composition disclosed herein. Non-sensitive liposomes can be loaded with contrast agent by employing any known technique, such as pH gradient loading, ionic gradient loading and osmotic loading. One method of loading non-sensitive liposomes is disclosed in the Laboratory Examples.

After a non-sensitive liposome composition has been administered to a subject (which can be performed by employing a method disclosed herein or known to those of ordinary skill in the art), a magnetic resonance image of a site of interest can be generated. As noted throughout the present disclosure, a magnetic resonance image can be generated by any known method and can be generated on any available MRI apparatus, such as a 2T whole-body clinical scanning instrument (e.g., a Signa Medical Systems scanner, available from General Electric of Milwaukee, Wis., United States of America).

In one example of the method, a single image can be generated at a time point known or suspected to permit enough time for the envirosensitive liposome composition to circulate through the subject's blood stream to a site of interest. In another example of the method, a time course series of images of a site of interest can be acquired, similar to the time course of images presented in FIGS. 2A and 2B. Such a time course of images can be focused on a particular region of interest, such as the brain, or on a biological structure known or suspected to have a vascular irregularity.

Continuing with the embodiment of the method, the presence of an in vivo blood pool can be detected by analyzing the magnetic resonance image. Such an analysis can comprise an evaluation of one or more MR images to identify the presence or absence of a blood pool at a particular site of interest. The presence of a blood pool is indicated, in a MR image, by the pixelation associated with a contrast agent. When images are black-and-white images, the contrast agent pixelation will show up as white pixelation.

As noted, the presence of a blood pool can be indicative of a vascular irregularity. A vascular irregularity can be, for example, a widening of a vascular structure. In one embodiment, a vascular irregularity can comprise an aneurysm. In another embodiment, a vascular irregularity can comprise an ischemic condition.

Ischemia/reperfusion injury is a significant source of morbidity and mortality in a number of clinical disorders, including myocardial infarction, cerebrovascular disease, and peripheral vascular disease. In addition, ischemia/reperfusion is relevant to the function of transplanted organs and to the recovery expedience following any cardiovascular surgery (see, e.g., Fan et al., (1999) *J. Mol. Med.* 77:577-596). Often times, ischemic conditions are not identified in a subject until after significant damage or death has resulted. Thus, the presently disclosed subject matter can be employed to monitor the formation, dissolution and properties of a blood pool, which can useful in the diagnosis and prevention of disorders related to vascular diseases and conditions.

V.D. Method of Generating a Heating Profile of a Site of Interest

In another aspect, a method of generating a heating profile of a site of interest is disclosed. The term "heating profile", as it is used herein, encompasses the heating of a region of tissue surrounding a site of heating. A heating profile reflects the increase and/or decrease in heat as a function of distance from the site of heating or from the source of heat (e.g., a heated catheter).

In one embodiment, the method comprises administering to a subject a thermosensitive liposome composition comprising: (i) a contrast agent and (ii) a thermosensitive liposome encapsulating the contrast agent and the compound of interest and having a melting temperature, $T_m$. Thermosensitive liposome compositions can be formed as described herein. The thermosensitive liposomes of such compositions will have a given melting temperature, which can be a function of the composition of the liposome. At temperatures below the $T_m$, the thermosensitive liposome retains its structural integrity; above the $T_m$, the thermosensitive liposome loses its structural integrity, allowing release of the liposome's contents. Representative contrast agents are described herein and can comprise, for example, $MnSO_4$.

Continuing with the method, a site of interest in a subject is then heated. Various methods of heating can be employed in the method, such as heating via a catheter warmed by passing hot water through the catheter. Other heating methods are described herein.

The release of the contrast agent from the thermosensitive liposome is then monitored using magnetic resonance imaging. The steps for acquiring such a magnetic resonance image are described herein. Standard MRI methodology can be employed in the acquisition of the image as disclosed herein and also will be known to those of ordinary skill in the art upon consideration of the present disclosure.

A heating profile of the site of interest can then be generated. In such a heating profile, the heating of an area to a temperature of at least $T_m$ can optionally be indicated by release of contrast agent at a periphery of the area. Such a heating profile can reflect the distance from a site of heating (e.g., the radial distance) at which the $T_m$ of the thermosensitive liposome is reached.

By way of example, a heated catheter can be employed to heat a tumor. The tumor tissue will be warmest near the site at which the catheter contacts the tumor, and will be cooler at points further away from the catheter. When the tumor tissue is homogeneous, this decrease in temperature as a function of distance from the catheter can reflect a linear or exponential decrease. At some distance from the catheter, the temperature of the tumor tissue will be equal to the $T_m$ of a given thermosensitive liposome composition. When thermosensitive liposomes reach this distance (as disclosed herein, envirosensitive (e.g. thermosensitive), and non-sensitive, liposomes accumulate at a site of heating) they melt and release their contents, namely a contrast agent. By evaluating MR images acquired as the thermosensitive liposomes approach the site of heating, the distance at which the $T_m$ of the liposomes is reached can be determined. At the distance from the catheter that the tissue is heated to $T_m$, contrast agent release will be immediate and will resemble a burst release. Thus distances equal to or less than the $T_m$ distance from the catheter can be identified, giving rise to a heating profile.

In another embodiment, two or more thermosensitive liposome compositions can be employed, for example, in succession. In this embodiment, the liposomes can have lipid compositions that impart different melting points. By administering several compositions, each with a different $T_m$, and compiling the results, a detailed heating profile, similar to a plot of different isotherms can be generated, which reflects the temperature of the tissue at various distances from the catheter or site of heating.

VI. Advantages of the Present Disclosure

The methods and compositions of the present disclosure offer many advantages over compositions, methods and approaches known and/or employed in state-of-the-art diagnostic and therapeutic procedures. Representative advantages of the present disclosure are described below. Other advantages will be apparent when considered in view of the present disclosure.

VI.A. Selectivity in Targeting

FIGS. 2A and 2B highlight several advantages of the methods and compositions of the presently disclosed subject matter. First, it is seen that in both of these figures, the contrast agent, and thus the compound of interest, is localized to the immediate region surrounding the tumor. There is no contrast agent detected in any region of this or any other slice in the immediate area of the tumor. This advantage of the presently disclosed methods and compositions is highlighted when FIG. 2A and particularly FIG. 2B are compared with FIG. 2C.

FIG. 2C is a MR image depicting the effect of infusing a rat bearing a flank tumor with a prior art contrast agent (MAG-NAVIST®, available from Berlex Laboratories, Wayne, N.J., United States of America). When this prior art contrast agent is injected into a rat having a flank tumor not heated by a catheter, the contrast agent is seen to associate not only with the tumor, but with other internal structures as well, including the presumably necrotic tissue in the center of the tumor and non-tumor flank tissue. This figure indicates that prior art contrast agents cannot be employed to specifically target the growing tissue (e.g., the periphery) of a tumor. Consequently, in contrast to the present disclosure, treatments based on this approach will suffer from a decreased concentration of a compound of interest (e.g., a chemotherapeutic agent) at the tumor, where the agent is most needed for therapeutic reasons.

Another related advantage of the methods and compositions disclosed herein is their size. The liposome compositions are typically about 120 nm in diameter. This small size ensures that the liposome compositions can be stably transported through the vasculature of a subject, while being large enough to evade trapping by the renal and/or hepatic systems and passing the normal vasculature wall.

VI.B. Rapid Clearance of Liposomes and Contrast Agent

One problem that can accompany the use of a contrast agent in a living organism is the toxicity of a contrast agent. If the contrast agent is not cleared from the system of a subject in a timely fashion, a toxic reaction can be initiated. This can be complicated by the occasional need to employ relatively high concentrations of contrast agent to generate an interpretable, high resolution image.

The presently disclosed methods and compositions do not suffer from this drawback. The liposome compositions can employ contrast agents that are highly effective at reducing proton relaxation times (i.e. T1's), and can therefore be employed in lower quantities than those that are toxic on a systemic basis. Additionally, in the present methods and compositions, the contrast agent is encapsulated by a liposome, which remains stable until it reaches a target site. Therefore, no contrast agent is released into the bloodstream of the subject as the liposomes travel to their target.

Figure 3A:
FIG. 3A is a MR image depicting several regions of interest (highlighted by white boxes) in which non-sensitive and thermosensitive liposome signal intensities were measured.
Figure 3B:
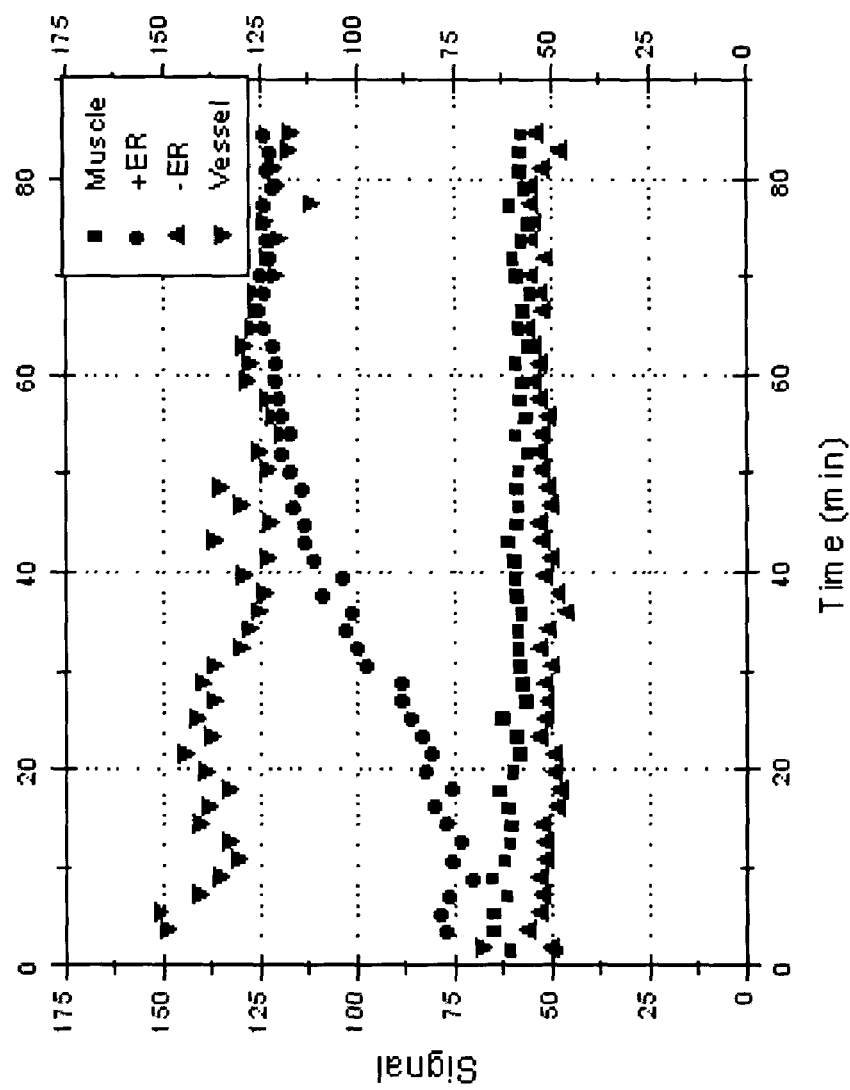
FIG. 3B is a plot depicting signal intensity for non-sensitive liposomes as a function of time for the regions highlighted in FIG. 3A. Solid squares correspond to signal detected in non-heated muscle; solid circles correspond to signal detected in an enhanced tumor region; solid triangles correspond to signal detected in a non-enhanced tumor region; and solid inverted triangles correspond to signal detected in the vessel.
Figure 3C:
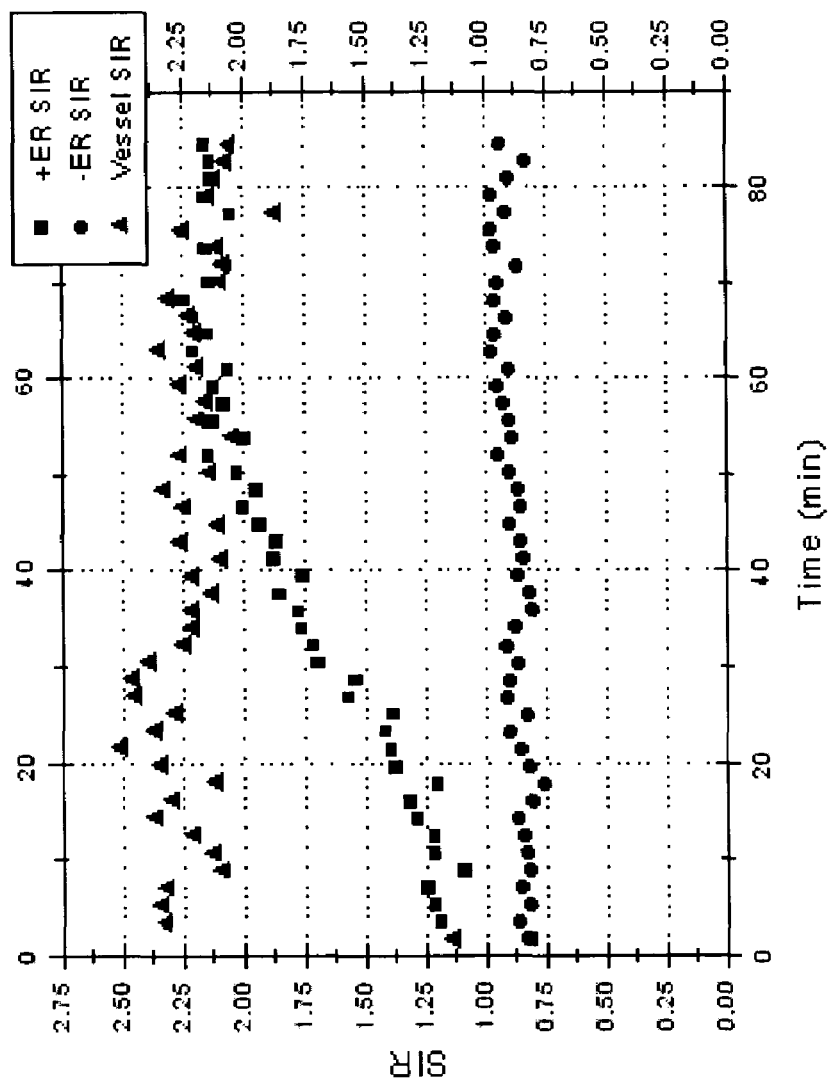
FIG. 3C is a plot depicting signal intensity ratio as a function of time for the non-sensitive liposomes. Solid squares correspond to the signal intensity ratio in an enhanced tumor region; solid circles correspond to the signal intensity ratio in a nonenhanced tumor region; and solid triangles correspond to the signal intensity ratio in the vessel.
Figure 3D:
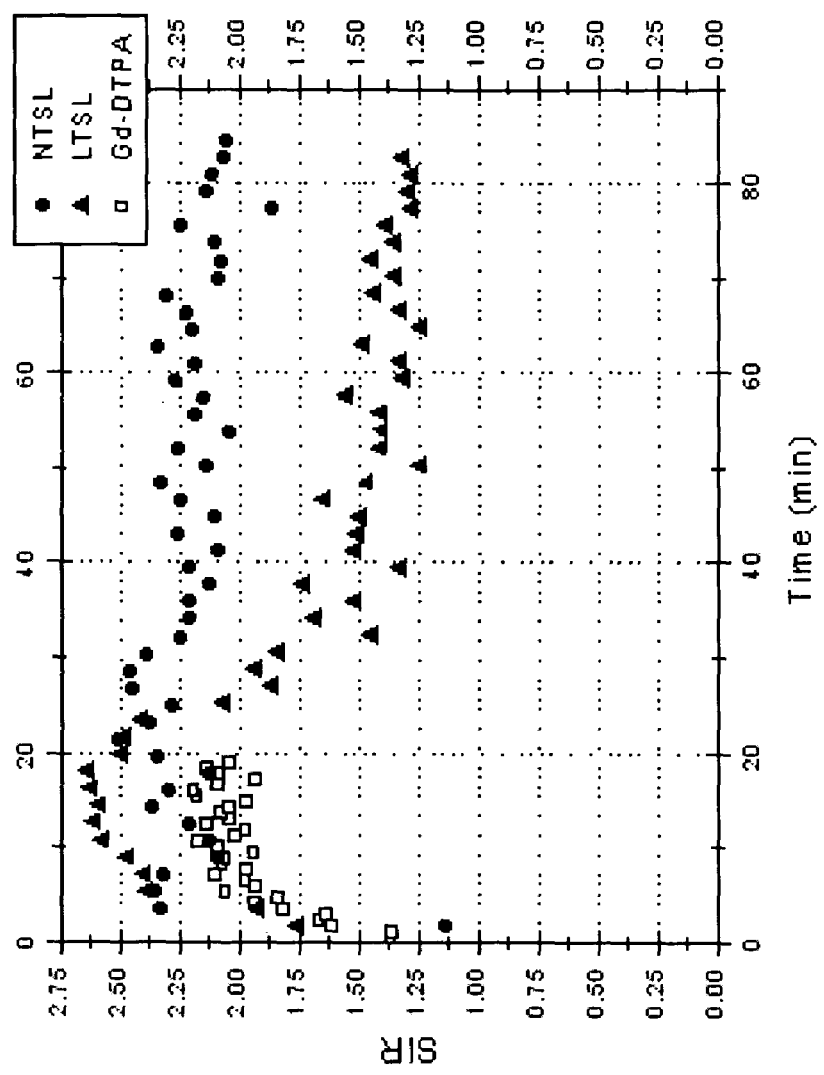
FIG. 3D is a plot depicting signal intensity ratio as a function of time as acquired from the femoral vein of the rat. Solid circles correspond to non-sensitive liposomes; solid triangles correspond to thermosensitive liposomes and open squares correspond to gadolinium-DPTA.

Moreover, as FIG. 3D indicates, the contrast agent is cleared from the circulatory system in about 90 minutes in the case of the thermosensitive liposomes and about 3-5 hours in the case of the non-sensitive liposomes. Additionally, the compositions and properties of these liposomes can be modified to vary their circulation time as desired.

VI.C. In Vivo Monitoring

Another advantage of the methods and compositions of the present disclosure is the ability to perform the methods in vivo. Often, diagnostic methods cannot be performed in vivo and are relegated, at least preliminarily, to artificial in vitro studies. In vitro conditions typically do not exactly reproduce in vivo conditions, particularly in the area of drug delivery and drug action/metabolism.

Another advantage is the ability to carry out the methods in a living organism. MRI is particularly suited to this application since it is a non-invasive, yet highly sensitive method. Thus, a study performed to monitor the delivery of a compound to a particular biological structure can be performed in vivo and a researcher can be confident that the observed results will be reproducible in similar living organisms.

VI.D. Real Time Monitoring

Yet another advantage of the present methods and compositions is the ability to perform real time monitoring of events occurring in vivo. A researcher can monitor, for example, the accumulation of liposome compositions at a heated site as the accumulation is occurring. The only delay is that delay associated with obtaining (for example, about 0.5-4 minutes, depending on scan settings) and processing (for example, less than about 3-6 seconds) the nucleus relaxation times to images.

This ability can be of great benefit in determining the time scale upon which events are occurring. This can translate into an estimate of the efficiency with which a given compound of interest is not only delivered to a site of interest, but also how the compound behaves once it has been delivered.

VI.E. A Site Can be Heated by Invasive/Noninvasive Techniques

In one aspect of the present disclosure, a site of interest is heated. Heating of the site of interest leads to the accumulation of liposome composition at the heated site over a period of time (FIGS. 2A-2B). Without heating the site of interest, the liposome might at best diffusely accumulate at the site (particularly if it is a tumor) for a brief time (FIG. 2E), or not at all (FIG. 2D). The site can be heated by invasive or non-invasive methods and can depend on the nature of the site being heated.

For example, in one aspect, a site (i.e., a tumor) is heated by inserting a catheter which is heated by circulating water, into the tumor mass. Other similar methods of invasive heating can be employed.

In other instances, it might be desirable to heat a site noninvasively. Such heating can be achieved by employing a method such as directing RF, IR, microwave or ultrasonic energy at the site. In these cases, it can be desirable to monitor the temperature of the heated site for thermal damage to the site.

In yet other instances, a laser can be employed to heat the site. Typically, when the site of interest is near the outer surface of the subject, such as on or near the skin, a laser, for example a laser emitting light at an IR frequency, can be employed to heat a site. In another example, the site is a subject's eye, and a laser can be employed to locally heat an exposed region of the eye.

VI.F. High Resolution Detection

One potential drawback to some MRI techniques is that the images generated are sometimes of low resolution due to a poor signal-to-noise ratio. To overcome this limitation, spatial resolution is sacrificed in order to have enough signal to generate an image. ESR, NMR and resonance frequency shift are several techniques that suffer from the lower S/N ratio or the use of different atom of excitation such as $^{13}C$. The presently disclosed methods and compositions, on the other hand, employ the protons of water. The effect of the contrast agent on these protons is minimal. The methods and compositions disclosed herein, on the other hand, routinely provide high resolution images of a site, as depicted in FIGS. 2A and 2B.

VI.G. Low Toxicity

A further advantage is the observation that the liposome compositions are relatively less toxic and/or damaging to a subject than other MR-based contrast agent-containing compositions. Some MR contrast agents, such as gadolinium-based contrast agents, can be toxic in large amounts. Often these amounts are required to generate high-quality images useful for diagnostic purposes.

Yet other imaging techniques require the use of radioactive compositions to monitor in vivo events, such as blood pool detection. Moreover these methods do not yield detailed high resolution images. For example, positron emission tomography (PET) is commonly employed, but cannot be employed to generate high resolution images. In another example, multiple-gated arteriography (MUGA) is typically employed in the study of left-ventricular function and wall motion of the heart. In MUGA, a subject's red cells are infused with $^{99}Tc$, a radioactive material. The radiation emitted from the $^{99}Tc$ is then detected and used to form an image of the blood pool within the subject's heart. Images can be acquired by employing a gamma camera, and data can be acquired at times of interest to a clinician or researcher. While MUGA has been effective, it requires the use of potentially damaging radioactive materials and can lead to toxic anaphylactic shock.

Yet other methods employ fluorescent dyes, which can themselves be toxic or can lead to undesirable conditions. Additionally, such approaches are limited to sites that are near an exposed surface of a patient, such as the skin or the surface of the eye.

The presently disclosed methods and compositions, on the other hand, employ contrast agents that can be less toxic to a subject. For example, Cu or Zn, which exhibit very low in vivo toxicity and good contrast agent properties, can be used. Even compounds that exhibit some toxicity, such as Mn, are safe to use in vivo with the presently disclosed methods and compounds, as the liposomes shield the contrast agent until the liposome loses structural integrity at the site of interest. Further, since the liposomes are targeted to a specific, less contrast agent is required to achieve results similar to or superior than those found when the contrast agent is administered at higher (potentially toxic) doses systemically.

LABORATORY EXAMPLES

The following Laboratory Examples have been included to illustrate representative modes. Certain aspects of the following Laboratory Examples are described in terms of techniques and procedures found or contemplated to work well in the practice of the presently disclosed subject matter. These Laboratory Examples are exemplified through the use of standard laboratory practices. In light of the present disclosure and the general level of skill in the art, those of skill will appreciate that the following Laboratory Examples are intended to be exemplary only and that numerous changes, modifications and alterations can be employed without departing from the spirit and scope of the present disclosure.

Laboratory Experiment 1

Liposome Formulation

Liposomes were made from either DMPC/Chol (55:45) mole per mole (mol/mol) or DSPC/Chol (55:45) (mol/mol) and were prepared by extrusion methods. Lipids, at the indicated ratios, were dissolved in chloroform, and then $^3$H-CHE was added to achieve approximately 10 μCi/100 mg lipid. The chloroform was removed under a gentle stream of nitrogen gas and, subsequently, the lipid samples were placed under a high vacuum for a time period of at least 4 hours to remove any residual solvent. The dried samples were hydrated (such that the final lipid concentration was approximately 100 mg/ml) with 300 mM citrate buffer, 300 mM $MnSO_4$ or 300 mM $MnCl_2$, adjusted to pH 3.5 by addition of hydrochloric acid. Following hydration, the multilamellar vesicles (MLVs) were subjected to five freeze-and-thaw cycles (freezing in liquid nitrogen and thawing at 40° C.). The resulting frozen and thawed MLVs were prepared to optimize the salt distribution across the lipid bilayers (Mayer et al., (1985) *Biochim. Biophys. Acta* 817: 193-196). The MLVs were extruded 10 times through stacked polycarbonate filters of 0.1 and 0.08 μm pore size at 40° C. using a water-jacketed Extruder™ (Northern Lipids, Inc., Vancouver, British Columbia, Canada). The mean size distribution of all liposome preparations was determined using a Nicomp Sub-micron Particle Sizer Model 270 (Pacific Scientific, Santa Barbara, Calif.) operating at 632.8 nm. The resulting liposome preparations typically exhibited an average diameter of approximately 100-120 nm. All liposomes, except those used for cTEM analysis and circular dichroism (CD) studies were radiolabeled. For these experiments, the phospholipid was quantitated using the Fiske and Subbarow (Fiske & Subbarow, (1925) *J. Biol. Chem.* 2: 375-395) phosphate assay. Briefly, 700 μl of 70% perchloric acid was added to lipid samples and heated to approximately 180-200° C. for 2 hours until the samples were colorless. Samples were cooled and 700 μl of Fiske reagent and 7 ml of ammonium molybdate was added and samples were subsequently reheated again to 100° C. for 20 min. Samples were cooled to room temperature and the absorbance was read at 820 nm.

Laboratory Example 2

Doxorubicin Encapsulation

Large unilamellar liposomes in buffer were fractionated on SEPHADEX® G-50 columns (Amersham Biosciences Corp., Uppsala Sweden) (1 ml sample volumes were placed on columns with at least a 20 ml column bed) equilibrated with various buffers at pH 7.5. The buffers used for the external environment included 25 mM HEPES/150 mM NaCl (HBS) for the liposomes with encapsulated 300 mM citrate and 300 mM sucrose/20 mM HEPES/15 mM EDTA (SHE) for the liposomes with encapsulated $MnSO_4$ and $MnCl_2$. The manganese sulfate-based procedure for doxorubicin loading was a modification of the method described by Cheung et al. (Cheung et al., (1998) *Biochim Biophys Acta* 1414(1-2): 205-16). In particular, it is noted that the solubility of 300 mM $MnSO_4$ is highly variable under the pH conditions described in the original procedure, presumably resulting in the formation of $Mn(OH)_2(S)$. In the studies reported here, liposomes were prepared in a 300 mM $MnSO_4$ (and $MnCl_2$) solution at a pH of 3.5; solutions that are stable for months at room temperature.

Following formation of the salt gradients as described above, the liposome lipid concentration was adjusted to 10 mg/ml and, subsequently, doxorubicin was added to achieve a drug-to-lipid ratio (wt/wt) of 0.2:1 at 20, 40 and 60° C. The accumulation of doxorubicin into liposomes was determined at the indicated time points by removing 100 μl aliquots and separating unencapsulated drug from encapsulated drug on 1 ml Sephadex G-50 (medium) spin columns equilibrated with the appropriate buffer. The concentration of doxorubicin in the excluded fraction was determined by measuring absorbance (at 480 nm) of a solution consisting of the sample, adjusted to 100 μl with HBS or SHE, to which 900 μl of 1% Triton X-100 was added. Prior to assessing absorbance at 480 nm, the sample was placed in >90° C. water bath until the cloud point of the detergent was observed. Liposome lipid concentrations were determined by adding a small aliquot of the excluded fraction to 5 ml of scintillation cocktail, where the radioactivity of the sample was subsequently determined by scintillation counting with the Packard 1900TR Liquid Scintillation Analyzer.

Laboratory Example 3

Sample Solution Formation

Liposomes made using the above procedure had their concentration converted to an equivalent $MnSO_4$ molarity using the molecular weight of the lipid and an assumption of a 1.2 μl/μmol$_{lipid}$ (Mayer et al., (1985) *Biochim. Biophys. Acta* 817 (1): 193-6) encapsulation volume commonly used to characterize liposome volume from concentration. Consequently, a 1 mg/ml lipid concentration with 300 mM $MnSO_4$ encapsulated concentration resulted in an overall $MnSO_4$ concentration of 0.437 mM for DPPC-MSPC-DSPE-PEG$_{2000}$ and 0.592 mM for DSPC/Chol for full liposome content release.

cl Laboratory Example 4

Manganese Sulfate Control Stock Solutions

Three control stock solutions of manganese sulfate ($MnSO_4 H_2O$), free DOX and $MnSO_4 H_2O$ in a molar ratio of 0.902:1 (DOX:Mn), and $MnSO_4.H_2O$ with thermally sensitive liposomes that were formed without the presence of $MnSO_4.H_2O$. These solutions, along with liposome solutions, were then diluted to concentrations from 0.25-8 mM. The solutions were placed in 5 ml NMR tubes cut to a three-inch length.

Laboratory Example 5

In Vitro MRI Scans

All MRI experiments were performed at the Center for In vivo Microscopy at Duke University in a 2-T 30-cm bore diameter magnet (Signa, G.E. Medical Systems, Milwaukee, Wis.). Temperature control within the bore was achieved with an automatic feed back control unit that was initially designed for maintaining temperature of laboratory animals (Qiu, (1997) *IEEE Trans. Biomed. Eng.* 44(11): 107-1113). Each experiment had six to eight sample tubes, which were contained within an exposed sample holder, and placed inside a 3.81 cm birdcage coil providing RF excitation. A temperature on the heating apparatus was chosen (at random for control experiments) and bore equilibration occurred within ten minutes. A series of $T_1$ images were then taken in the axial plane with a field of view of 5 cm at excitation times ($T_e$) of 8 ms and repetition times ($T_r$) of 20, 33.3, 66.6, 150, 316, 633, and 1266 msec. Between six and eight temperature relaxivity measurements were obtained. Each experiment was repeated three times with independent formulated reagents. Liposomes were tested sequentially with a minimum of two measurements below-above-and-back below the transition temperature for the LTSL. The NTSLs were tested in the same manner to illuminate any possible hysteresis.

Images that were obtained were analyzed by selecting a region of interest and measuring average intensity for each sample dilution. Intensity data were fit using non-linear least squares data fitting governed by the Gauss-Newton method, MATLAB® (The MathWorks, Inc., Natick, Mass., United States of America), to obtain a $T_1$ for each concentration tested. Reciprocal $T_1$ data were plotted as a function of concentration and fitted to a linear regression yielding relaxivity (mM sec)$^{-1}$ as the slope. Relaxivity was plotted as a function of temperature.

Laboratory Example 6

In Vivo Experiments

Fibrosarcocomas were transplanted in the flank of fisher 344 rats and allowed to grow to 17-19 mm in diameter. Rats were anesthetized with pentobarbital (source/amount) and a 16 gauge catheter was placed through the center of the tumor. Heated water (56° C., 1.8 ml/s) was passed through the catheter to provided hyperthermia. During MRI scans, the heating water was doped with 0.25 M $MnSO_4$ to prevent flow image artifacts. Gradient recalled echo was used with a $T_r$ of 23 ms, $T_e$ of 1.4 ms, and flip angles of 5, 15, 30, 40, 50, 60 degrees for the initial $T_1$ weighted image. Subsequent drug uptake scans were performed at a flip angle of 33°. 3D volume images, 12 slices 1 mm thick, were taken with a field of view of 6 cm with a pixel size of 234×234 μm. Four and signal image averaging was used for liposome and Gd-DTPA experiments yielding scan times of 1 min, 45 sec and 30 sec respectively.

1NEX image averaging was used for the first twenty minutes of liposome or Gd uptake. Subsequent images were taken at 4NEX for the remainder of the experiment (90-120 minutes).

Results and Discussion of Laboratory Examples 1-6

Figure 1B:
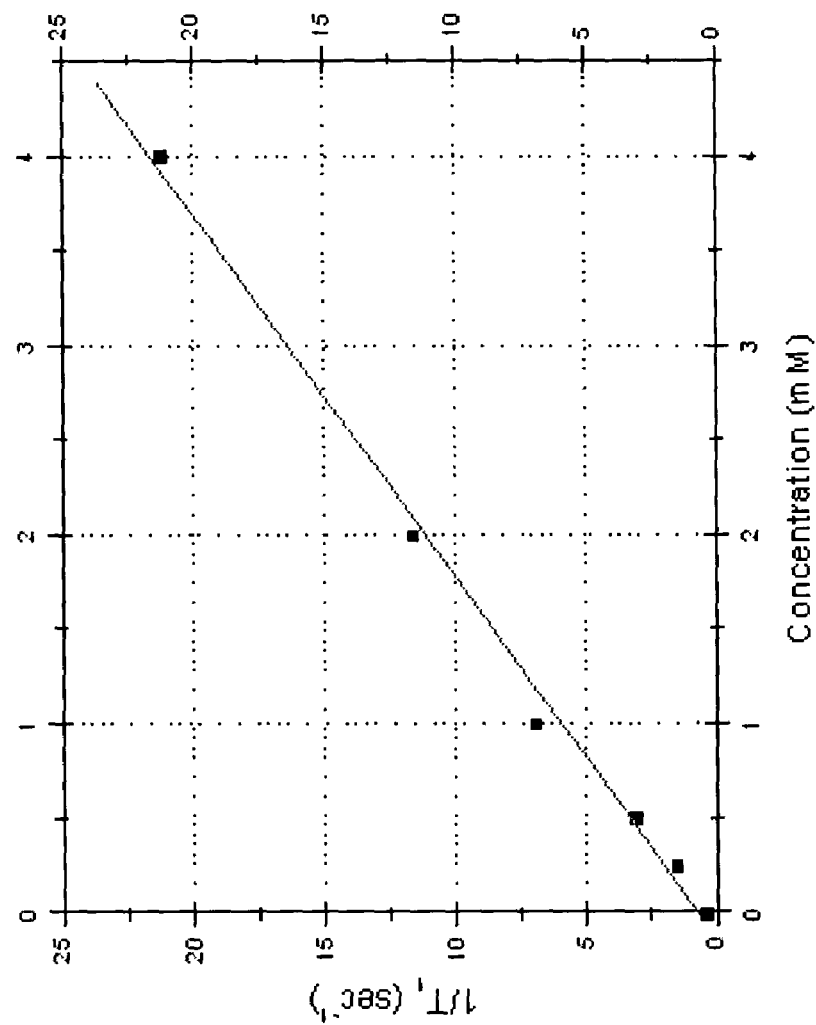
FIG. 1B is a plot depicting the relationship between $1/T_1$ and contrast agent concentration for the same formulations described in FIG. 1A. The slope of the line is a measure of the $(T_1)$ relaxivity of the system.

To quantify the concentration of drug in vivo using MRI, in vitro experiments were performed to determine the concentration- and temperature-dependence of $T_1$ shortening. These experiments measured signal intensity resulting from proton spin realignment to the bulk magnetic field after excitation from repetitive radio frequency pulses. The signal received is dependent on the repetition times ($T_r$) between RF pulses. This dependency of signal on $T_r$ is illustrated in FIG. 1A. $MnSO_4$ liposome-DOX formulation measured over a range of drug concentrations (T=29.9° C.). The curves shown in FIGS. 1A-1D are governed by Equation 1. The data were fit to this equation to obtain relative proton density (PD), relaxation time constant ($T_1$), and baseline noise (C) for each concentration/temperature combination:

$$\text{signal} = PD\left(1 - \exp\left(\frac{-Tr}{T1}\right)\right) + C \quad \text{Equation 1}$$

The rate of rise of the signal versus $T_r$ (shortening of $T_r$ increases with drug concentration) (FIG. 1). Changes in the curve's asymptotic value, PD, are governed by the number of protons in a sample and by the effects of $T_2$. There is a linear relationship between the reciprocal of $T_1$ ($1/T_1$) and the $MnSO_4$ concentration, and the slope of this line is termed "relaxivity" (mM·sec)$^{-1}$ (FIG. 1B). It is possible to determine in vivo $MnSO_4$ concentration by measuring $T_1$ shortening and using the in vitro calibration for relaxivity (Lyng, (1998) *Mag. Reson. Med.* 40(1): 89-98). Since the molar ratio between $MnSO_4$ and DOX is known for the liposome formulations, one can then determine DOX concentration.

Figure 1C:
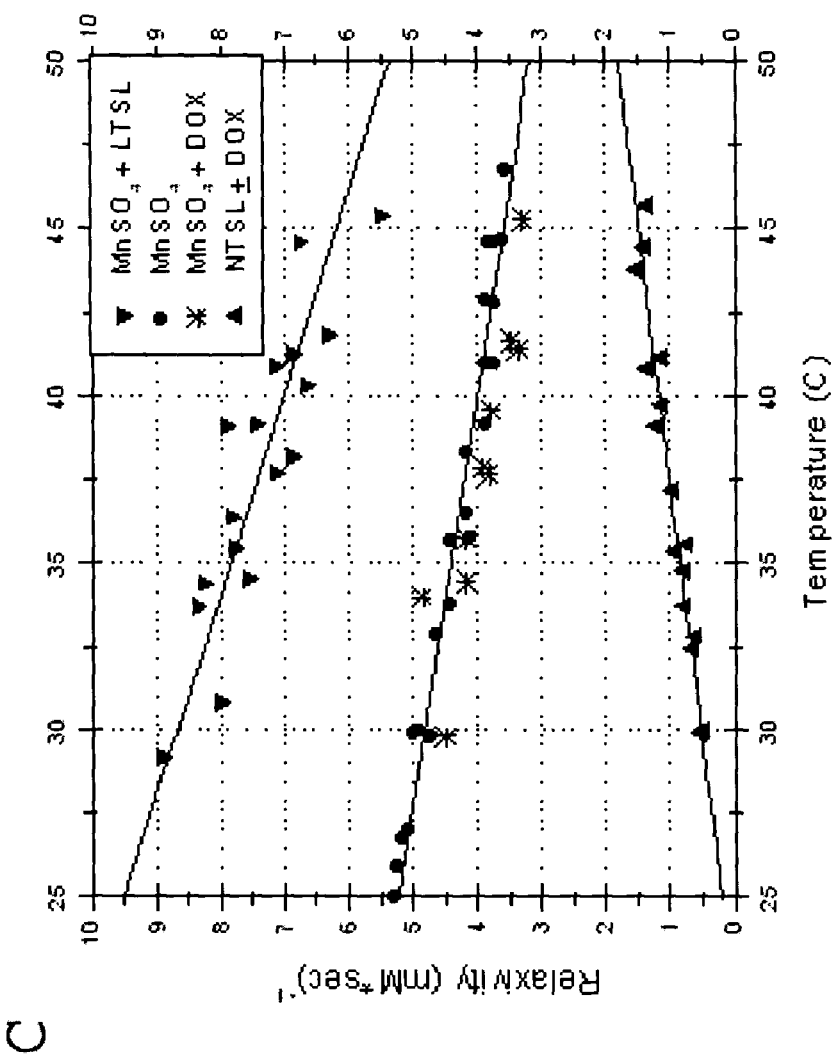
FIG. 1C is a plot depicting the effect of temperature on relaxivity. In this figure inverted solid triangles represent thermosensitive liposomes loaded with contrast agent in the exterior buffer; solid circles represent free contrast agent; stars represent free contrast agent and DOX at a concentration ratio identical to that found in the liposome; and solid triangles represent non-sensitive liposomes loaded with DOX and also represent empty non-sensitive liposomes.

Relaxivity was measured for $MnSO_4 \pm DOx$, free $MnSO_4$+ empty low temperature sensitive liposomes (LTSL), and $MnSO_4 \pm DOX$ loaded into non-thermally-sensitive liposomes (NTSL) over a range of temperatures and drug concentrations. Relaxivity changed as a function of temperature, but this relationship was different for free $MnSO_4 \pm DOX$ and the NTSL (FIG. 1C). $MnSO_4$+ empty LTSL and free $MnSO_4 \pm DOX$ exhibit decreased relaxivity with increased temperature, presumably due to increased thermal motion of $H_2O$ and Mn. This increased thermal motion reduces their interaction, thereby limiting the ability of Mn to shorten $T_1$. $MnSO_4$+DOX and $MnSO_4$−DOX have identical relaxivity profiles indicating that DOX, at a concentration expected to be seen in vivo, has no effect on this relationship. In contrast, relaxivity of NTSL±DOX increases as temperature is raised. This inverted temperature dependence might be due to an increase in liposome permeability causing an increase in water exchange across the lipid bilayer (Fossheim, (1999) *Magn. Reson. Imaging* 17(1): 83-9; Bacic, (1988) *Magnet. Reson. Med.* 6(4): 445-58).

Linear regressions for relaxivity as a function of temperature were obtained for all in vitro samples (FIG. 1C). $MnSO_4$+LTSL, $MnSO_4$, and NTSL±DOX had slopes±S.E. of −166±0.023, −0.082±0.003, and 0.064±0.005 (mM sec ° C.)$^{-1}$ and intercepts±S.E. of 13.67±0.087, 7.28±0.12, −1.41+0.18 (mM·sec)$^{-1}$, respectively. These results are similar to previous results reported for free $MnCl_2$ and comparable to other liposome formulations using Gd either loaded into the liposomes and/or bound to its surface (Suga, (2001) *Invest. Radiol.* 36(3): 136-45; Fossheim, (1999) *Magn. Reson. Imaging* 17(1): 83-9; Unger, (1993) *J. Mag. Res. Imag.* 3: 195-198; Schwendener, (1990) *Invest. Radiol.* 25(8): 922-32; Niesman, (1990) *Invest. Radiol.* 25(5): 545-51). For comparison, Gd-DTPA (MAGNAVIST™) has a relaxivity of approximately 4-4.5 (mM·sec·° C.)$^{-1}$ (Unger, (1993) *J. Mag. Res. Imag.* 3: 195-198) at physiological temperatures compared to 4.25 (mM·sec·° C.)$^{-1}$ for the LTSL.

Figure 1D:
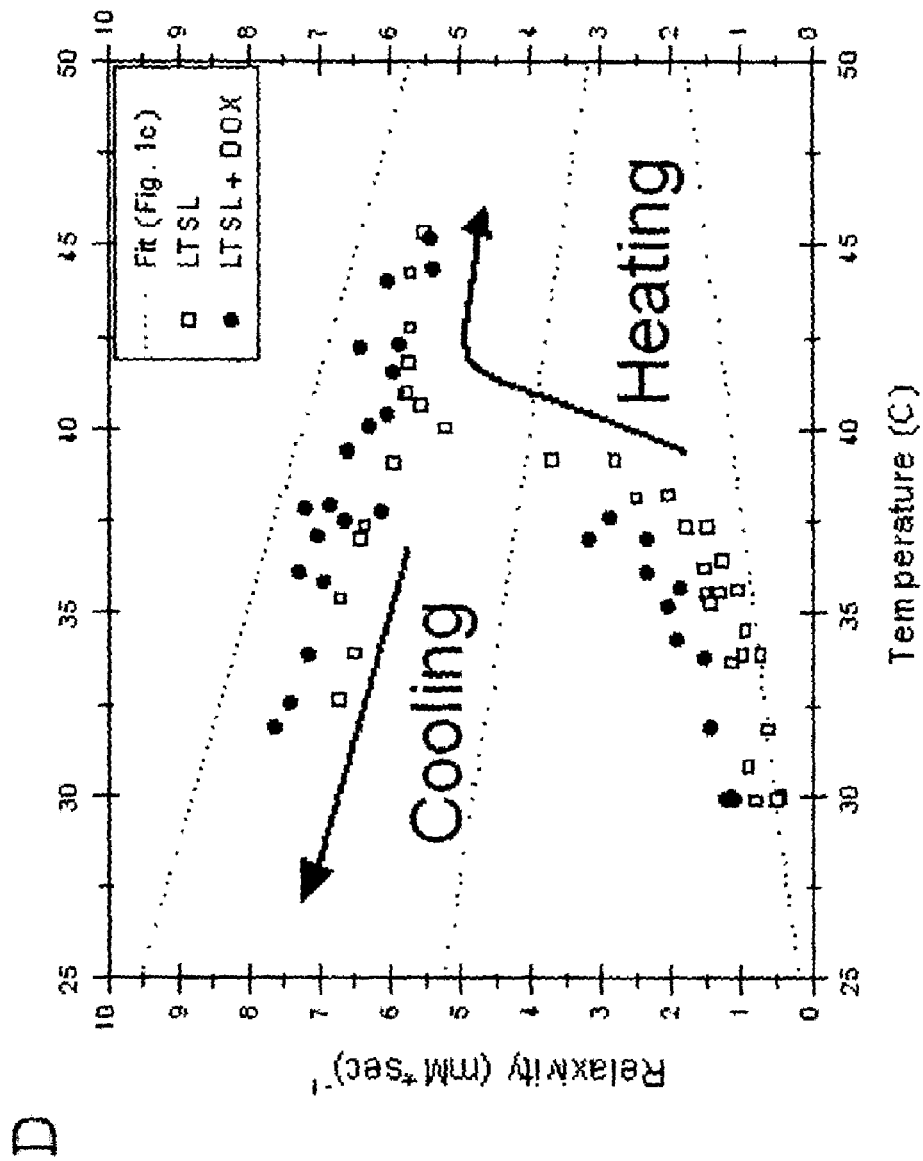
FIG. 1D is a plot depicting the effect of temperature on relaxivity of thermosensitive liposomes as the composition is heated and cooled. In this figure, open squares represent thermosensitive liposomes and closed circles represent thermosensitive liposomes loaded with DOX. Heating and cooling operations are indicated and progress from 30° C. to 45° C. and back to about 32° C. are depicted.

The relaxivity measurements for the LTSL are measured over a range of temperatures between 30 and 45° C. showing a complex relationship (FIG. 1D). These measurements were taken at several temperature points below and above the transition temperature for this liposome formulation (38-40° C.), which is the temperature at which the liposome goes from solid to liquid phase (Needham, (2000) *Cancer Res.* 60(5): 1197-201; Magin, (1984) *Cancer Drug Delivery* 1(2): 109-17). Measurements were started below the transitions temperatures, escalated beyond the transitions, and then were repeated as the solutions were cooled back below the transitions (see arrows, FIG. 1D). During initial heating period, LTSL had relaxivity values similar to those of the NTSL. When the phase transition temperature for LTSL was approached, however, relaxivity dramatically raised to levels nearly equivalent to those for free MnSO$_4$+ empty LTSL. This was not unexpected as content release from the LSTL formulation happens within seconds of reaching these temperatures, occurring in a burst like manner (Needharn, (2000) *Cancer Res.* 60(5): 1197-201). These relaxivity measurements support the previous reports that drug release from this liposome occurs just below the transition temperature (Needham, (2000) *Cancer Res.* 60(5): 1197-201; Magin & Niesman, (1984) *Canc. Drug Del.* 1(2): 109-17). Once release of liposomal contents occurred, further heating showed decreased relaxivity, consistent with levels seen for free MnSO$_4$ in solution. Relaxivity increased during subsequent cooling in a manner parallel to MnSO$_4$+ empty LTSL; the relaxivity slope of MnSO$_4$ loaded into LTSL, post release, was $-0.157\pm0.0167$ (mM·sec·° C.)$^{-1}$ which is the same as that of MnSO$_4$+ empty LTSL at $-0.166\pm0.023$ (mM·sec·° C.)$^{-1}$. However, the intercepts for LTSL and the MnSO$_4$+ empty LTSL are somewhat different, suggesting that the liposomes did not release all of their contents. The absence of complete content release from the LTSL formulation has been reported (Needham, (2000) *Cancer Res.* 60(5): 1197-201).

The liposome formulations were studied in fibrosarcomas implanted in the flank of Fisher 344 rats. The center of the tumor was heated using a catheter through which hot was water circulated. This heating system provided a radial temperature distribution, the profile of which is predicted by the 1D steady state heat equation (insert FIG. 2A, timepoint 1). Steady state temperature distributions were reached after 30 minutes of HT treatment. Liposomes were then administered intravenously, followed by MR imaging.

MR imaging following NTSL administration demonstrated signal enhancement in the tumor when treated with HT (see FIG. 2A), but not with NTSL administration in the absence of HT (see FIG. 2D). Enhanced signal intensity was initially seen in relatively large vessels immediately after injecting liposomes. These vessels remained visible throughout the course of the experiment (90 minutes). This result verifies that these sterically stabilized liposomes have a relatively long circulation time. Signal enhancement progressively increased in the tumor, consistent with time dependent liposome accumulation. There was clear heterogeneity in enhancement, presumably due to heterogeneity in blood perfusion and/or vessel pore size (Kong et al., (2001) *Cancer Res.* 61(7): 3027-32). There was no enhancement in adjacent normal tissue, suggesting delivery was limited to tissues that were heated.

The results obtained for the LTSL are different from those for the NTSL. As shown in FIG. 2B at identical time intervals, vessel enhancement is also seen with the LTSL as it was with the NTSL, but its intensity begins to decrease after 15-20 minutes. FIG. 2E shows that without heating, a less intense but more uniform signal enhancement occurs, but then rapidly fades after five minutes as clearance from the vasculature occurs. Unlike the NTSL, the LTSL showed strong signal enhancement at the tumor periphery as well as within the tumor parenchyma. Again, although it is not the inventors desire to be bound to any particular theory of operation, it is speculated that the enhancement at the edge of the tumor might be due to the higher vascular density in such regions or intravascular release as liposomes approach the tumor. The temperature at the tumor capsule is between 38.5-41° C., which is high enough to cause MnSO$_4$ and DOX release. There is minimal enhancement of surrounding tissue using the LTSL, further supporting the premise that delivery of the liposome and/or its contents had occurred preferentially in the heated zone. Experiments were also performed using NTSL and LTSL without HT. In this case, signal enhancement was not seen in any tissue.

Serial measurements of signal enhancement following Gd-DTPA injection are shown in FIG. 2C as a typical contrast MR image (without HT) for comparison with liposome results. The panels represent 0, 0.5, 5, and 15 minutes post injection. The rate of signal enhancement occurs over a shorter time scale than with liposomes. Enhancement occurs in all tissues with a high degree of non-uniformality in the tumor. This distribution pattern can be attributed to the high vascular permeability of Gd-DTPA as a result of its low molecular weight (508 g/mol).

In vivo drug relative concentrations were performed by signal intensity image analysis over regions of interest (ROI) within heated tumors. The white boxes present in FIGS. 2A, 2B and 2C indicate these ROIs. ROIs in the tumor represent an enhanced tumor region, +ET, where signal enhancement occurred and a non-enhanced tumor region -ET, where image enhancement did not occur (FIG. 3B). Muscle in the non-tumor bearing leg of the animal was used as a non-heated, normal tissue control. ROI signal intensities for NTSL were normalized with muscle in the non-tumor bearing leg to yield a signal intensity ratio (SIR) (Takehara et al., (2001) *Br. J. Cancer* 84(12): 1681-5). The procedure was repeated for the LTSL and the Gd-DTPA and the SIR for the vessel, tumor enhancing region, and the non-tumor enhancing region is shown in FIGS. 3D, 3E, and 3F, respectively.

SIR calculations were also performed on the femoral vein in the NTSL, LTSL and Gd-DTPA experiments (see FIG. 3D). Femoral vessel SIR for NTSL increased to a value of 2.25 at 10-15 minutes and remained constant throughout the experiment, consistent with a long circulation time. Femoral vessel SIR for the LTSL shows a rise to 2.5 at 15-20 minutes and subsequent drop off toward base line levels by 60 minutes post injection. This decrease in LTSL SIR might be due to a relatively short circulation time, which has been documented in previous studies. Gd-DTPA also shows a rapid increase to a plateau value of a SIR equal to 2.0 after 10 minutes. This value remains constant through the course of the experiment but would decrease if the experiment had been followed long enough for the contents to wash out of the tissue. It is documented that 83%±14% of the Gd-DTPA is excreted in urine in about 6 hours. The mean elimination half-life of Gd-DTPA is about 0.2±0.13 hours. (Berlex Imaging MAGNAVIST® package insert).

Figure 3E:
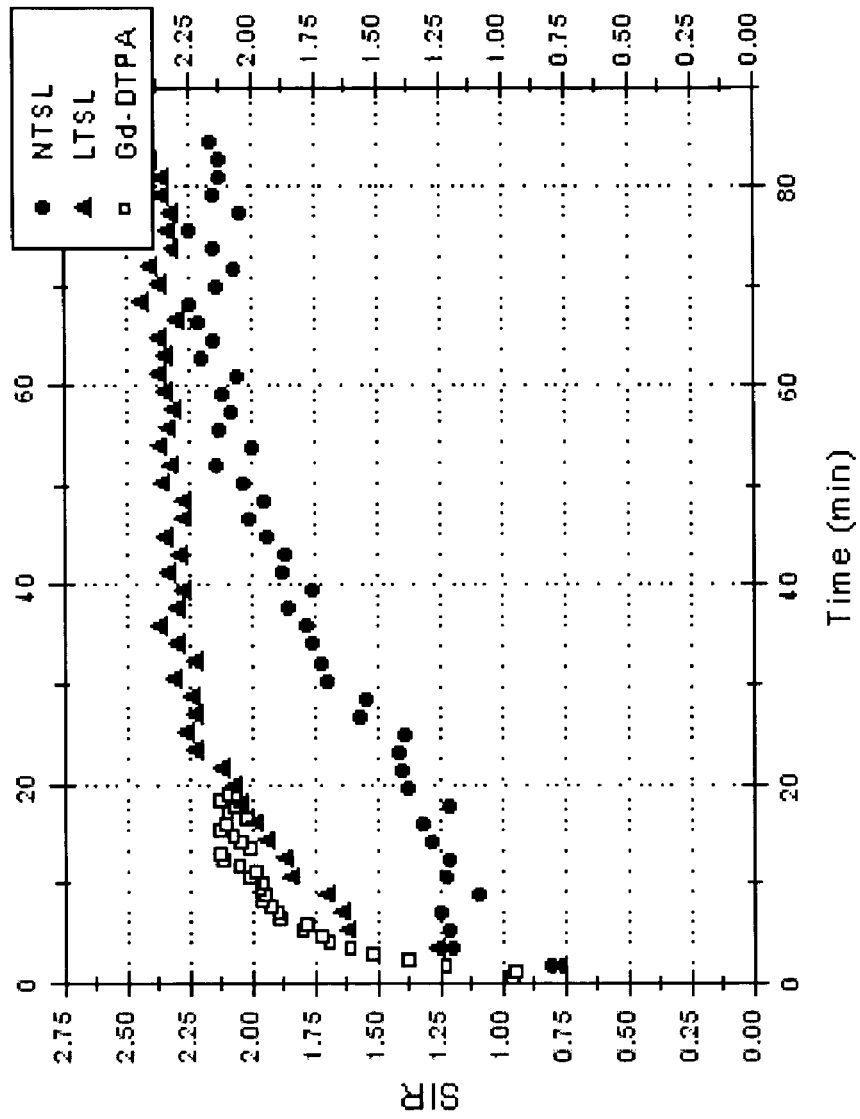
FIG. 3E is a plot depicting signal intensity ratio as a function of time in enhanced regions of the tumor. Solid circles correspond to non-sensitive liposomes; solid triangles correspond to thermosensitive liposomes; and open squares correspond to gadolinium-DPTA.

All tumor-enhancing regions tended to reach the same SIR plateau value of 2-2.25, but the rate at which they reached the plateau was different (see FIG. 3E). Gd-DTPA reached a plateau by 10 minutes and remained constant up to 20 minutes. The NTSL had the slowest rise reaching a plateau after 50 minutes, and a maximum of 2.25 after 70 minutes. LTSL had an intermediate response rising to a value of 2 after 20 minutes and a maximum of 2.25 after 30 minutes. The rapid increase of the SIR for Gd-DTPA can be attributed to the small size of the contrast agent. Vascular permeability to molecules than 1000 MW is dominated by the concentration gradient across the vessel wall (Yuan et al., (1995) *Cancer Res.* 55: 3752-6; Yuan et al., (1994) *Cancer Res.* 54: 3352-56). At 508 g/mol Gd-DTPA is highly permeable to the vessel walls. The lower rate of increasing SIR for the NRSL is attributed to the relatively low permeability of the liposomes through the vessel. The rapid release kinetics of the LTSL (50% drug release <20 seconds) indicates that at least some of the drug is released intravascularly (Kong et al., (2000) *Cancer Res.* 60(24): 6950-7). Therefore, the formulation is expected to show SIR kinetics that are intermediate between that of the free contrast agent and the NTSL, which is not thermally sensitive.

Figure 3F:
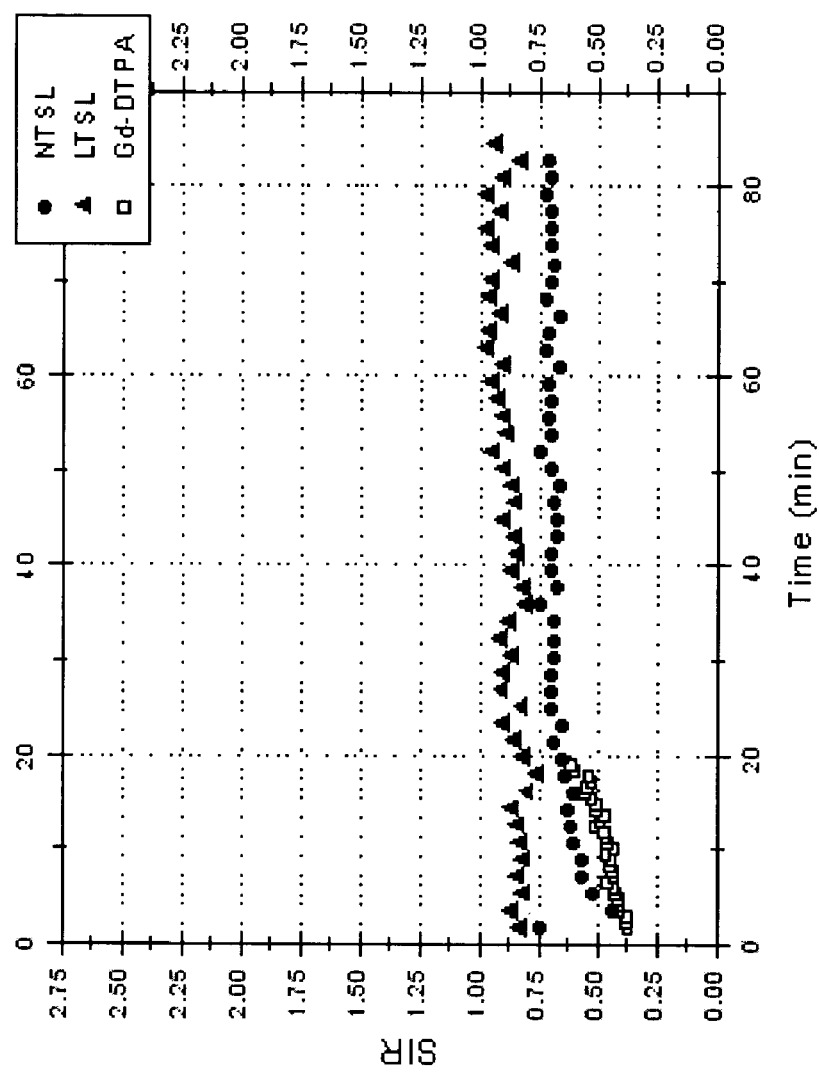
FIG. 3F is a plot depicting signal intensity ratio as a function of time for a nonenhanced tumor region. Solid circles correspond to non-sensitive liposomes; solid triangles correspond to thermosensitive liposomes; and open squares correspond to gadolinium-DPTA.

The non-tumor enhancing region, FIG. 3F, shows qualitatively similar results when comparing NTSLs with Gd-DTPA experiments. Both experiments have SIRs that rise to 0.4 to 0.6 after 20 minutes. The NTSL SIR remains constant thereafter. The SIR for the LSTL remains constant through the entire experiment. The difference for this response might be due to the rapid release of LTSL contents creating a concentration gradient that drives delivery into regions of the tumor that are poorly perfused.

Laboratory Examples 1-6 demonstrate the ability to image $MnSO_4$ encapsulated within thermally sensitive and non-sensitive liposomes. Additionally these Laboratory Examples show that content release from the liposomes is also imageable. These Laboratory Examples demonstrate the distribution of NTSL and LTSL liposomal drug delivery in animal studies. These results are applicable to other drugs encapsulated in this particular liposome. Because the labeling agent is required for the drug loading, other liposome/drug formulations are possible and can be similarly used for real time monitoring of drug delivery. By employing an in vitro approach, such as that performed in the Laboratory Examples presented herein, quantification of drug concentration distribution can be obtained. This ability allows for monitoring of liposomal drug delivery in individual patients, leading to individualized treatment, which can increase overall efficacy.

REFERENCES

The references listed below as well as all references cited in the specification are incorporated herein by reference to the extent that they supplement, explain, provide a background for or teach methodology, techniques and/or compositions employed herein.

Abraham et al., (2002) *Biochim. Biophys. Acta* 1565: 59-72
Bacic et al., (1988) *Magn. Reson. Med.* 6(4): 445-58
Bogdanov et al., (1993) *Radiology* 187: 701
Bondurant et al., (2001) *Biochimica et Biophysica Acta* 1511: 113-122
Cheung et al., (1998) *Biochim Biophys Acta* 1414(1-2): 205-16
Dessler et al., (1994) *Invest. Radiol.* 29 supl. 2: S65
Fan et al., (1999) *J. Mol. Med.* 77:577-596
Fossheim, (1999) *Magn. Reson. Imaging* 17(1): 83-9
Gregoriadis et al.; (1980) *Receptor-mediated Targeting of Drugs*, Plenum Press, New York, pp. 243-266
*Harrison's Principles of Internal Medicine* (Fauci et al., Eds.) 14th Ed. McGraw-Hill, New York, p. 84 (1998)
Kakinuma et al., (1996) *Int. J. Hyperthermia* 12(1): 157-165
Kean & Smith, (1986) *Magnetic Resonance Imaging: Principles and Applications*, Williams and Wilkins, Baltimore, Md.
Knight; *Liposomes: From physical structure to therapeutic applications*, Elsevier, North Holland, pp. 310-311 (1981)
Kong et al., (2000) *Cancer Res* 60(24): 6950-7
Kong, et al. (2000) *Cancer Res.* 60(16): 4440-5
Kong et al., (2001) *Cancer Res.* 61(7): 3027-32
Kong & Dewhirst, (1999) *Int. J. Hyperther.* 15(5): 345-70
Litzinger & Huang, (1992) *Biochim Biophys Acta* 1113: 201-227
Lokling et al., (2001) *Magn. Reson. Imag.* 19: 731-738
Lokling et al., (2003) *Magn. Reson. Imag.* 21:531-540
Lyng et al., (1998) *Magn. Reson. Med.* 40(1): 89-98
Magin & Niesman, (1984) *Canc. Drug Del.* 1(2): 109-17
Mayer et al., (1985) *J. Biol. Chem.* 260(2): 802-808
Meyer et al., (1994) *Invest. Radiol.* 29 supl. 2: S90
Mueller et al., (2000) *Macromolecules* 33: 4799-4804
Naoi & Yagi, (1984) *Biochem. Int.* 9: 267-272
Needham et al., (2000) *Cancer Res.* 60(5): 1197-201
Niesman et al., (1990) *Invest. Radiol.* 25(5): 545-51
Ogan et al., (1987) *Invest. Radiol.* 22: 665
Papahadjopolous, (1979) *Ann. Rep. Med. Chem.* 14: 250-260
Qiu et al., (1997) *IEEE Trans. Biomed. Eng.* 44(11): 1107-1113
Schumann-Giampieri et al., (1991) *Invest. Radiol.* 26: 969
Schwendener et al., (1990) *Invest. Radiol.* 25(8): 922-32
Senior et al., (1985) *Biochim. Biophys. Acta* 839: 1-8
Shen et al., (1994) *Invest. Radiol.* 29 supl. 2: S217
Spratt et al., (2003) *Biochimica et Biophysica Acta* 1611: 35-43
Suga et al., (2001) *Invest. Radiol.* 36(3): p. 136-45
Surolia & Bachhawat, (1977) *Biochim. Biophys. Acta* 497: 760-765
Takehara et al., (2001) *Br. J. Cancer* 84(12): 1681-5
Unger et al., (1993) *J. Mag. Res. Imag.* 3: 195-198
Vexler et al., (1994) *Invest. Radiol.* 29 supl. 2: S62
Wang et al., (1990) *Radiology* 175: 483
Yatvin et al., (1978) *Science* 202: 1290
Yuan et al., (1994) *Cancer Res.* 54: 3352-56
Yuan et al., (1996) *Cancer Res.* 55: 3752-56
U.S. Pat. No. 5,094,854
U.S. Pat. No. 5,464,696
U.S. Pat. No. 5,833,948
U.S. Pat. No. 5,888,476
U.S. Pat. No. 5,925,987
U.S. Pat. No. 5,961,953
U.S. Pat. No. 6,010,681
U.S. Pat. No. 6,200,598
WO92/21017

It will be understood that various details disclosed herein may be changed without departing from the scope of the disclosure. Furthermore, the foregoing description is for the purpose of illustration only, and not for the purpose of limitation.

What is claimed is:

1. An in vivo method of monitoring the localization and distribution of a compound of interest to a desired site in an organism by magnetic resonance imaging, the method comprising:
   (a) administering an envirosensitive liposome composition to a subject, the composition comprising:
      (i) a contrast agent;
      (ii) a compound of interest; and
      (iii) an envirosensitive liposome encapsulating the contrast agent and the compound of interest; and
   (b) monitoring the localization and distribution of the compound of interest to a desired site by magnetic resonance imaging, wherein the monitoring comprises monitoring release of the contents of the liposome at the desired site by monitoring an increase in the presence of the contrast agent released from the liposome at the desired site as the contents of the liposome are being released at the desired site.

2. The method of claim 1, further comprising increasing blood flow to the desired site.

3. The method of claim 2, wherein the increasing blood flow comprises heating the desired site.

4. The method of claim 3, wherein the increasing blood flow is by a method selected from the group consisting of contacting a heated catheter with the desired site, applying RF or microwave energy to the site, applying ultrasonic energy to the site and applying a laser beam to the site.

5. The method of claim 1, wherein the envirosensitive liposome is a liposome selected from the group consisting of a thermosensitive liposome, a pH-sensitive liposome, a chemosensitive liposome and a radiation-sensitive liposome.

6. The method of claim 5, wherein the thermosensitive liposome comprises a formulation selected from the group consisting of DPPC-PEG$_{2000}$, DPPC-DSPE-PEG$_{2000}$ (95:5, mol:mol); DPPC-MSPC-DSPE-PEG$_{2000}$ (90:10:4, mol:mol).

7. The method of claim 1, wherein the desired site is a tumor.

8. The method of claim 1, wherein the contrast agent comprises a element selected from the group consisting of Gd, Cu, Cr, Fe, Co, Er, Ni, Eu, Dy, Zn, Mg, Mo, Li, Ta, and Mn.

9. The method of claim 1, wherein the compound of interest is a chemotherapeutic agent.

10. The method of claim 1, further comprising exposing the envirosensitive liposome at the desired site to a non-physiological environmental condition.

11. The method of claim 10, wherein the environmental condition is selected from the group consisting of hyperthermia, electromagnetic radiation, a chemical agent and non-physiological pH.

12. A method of monitoring the accumulation of a compound of interest at a desired site in vivo by magnetic resonance imaging, the method comprising:
(a) administering to a subject an envirosensitive liposome composition comprising:
(i) a contrast agent;
(ii) a compound of interest; and
(iii) an envirosensitive liposome encapsulating the contrast agent and the compound of interest; and
(b) monitoring the accumulation of the compound of interest at a desired site by magnetic resonance imaging, wherein the monitoring comprises monitoring release of the contents of the liposome at the desired site by monitoring an increase in the presence of the contrast acient released from the liposome at the desired site as the contents of the liposome are being released at the desired site.

13. The method of claim 12, wherein the site of interest is selected from the group consisting of a tumor, injury site, and tissue edema.

14. The method of claim 12, wherein the envirosensitive liposome is a liposome selected from the group consisting of a thermosensitive liposome, a pH-sensitive liposome, a chemosensitive liposome and a radiation-sensitive liposome.

15. The method of claim 14, wherein the thermosensitive liposome comprises a formulation selected from the group consisting of DPPC-PEG$_{2000}$, DPPC-DSPE-PEG$_{2000}$ (95:5, mol:mol); DPPC-MSPC-DSPE-PEG $_{2000}$ (90:10:4, mol:mol).

16. The method of claim 12, wherein the contrast agent comprises a element selected from the group consisting of Gd, Cu, Cr, Fe, Co, Er, Ni, Eu, Dy, Zn, Mg, Mo, Li, Ta, and Mn.

17. The method of claim 12, wherein the compound of interest is a chemotherapeutic agent.

18. The method of claim 12, wherein there is increased blood flow to the desire.

19. A method of generating a heating profile of a site of interest, the method comprising:
(a) administering to a subject a thermosensitive liposome composition comprising:
(i) a contrast agent; and
(ii) a thermosensitive liposome encapsulating the contrast agent and the compound of interest and having a melting temperature T$_m$;
(b) heating a site of interest in a subject;
(c) monitoring release of the contrast agent from the thermosensitive liposome using magnetic resonance imaging, wherein the monitoring comprises monitoring release of the contents of the liposome at the desired site by monitoring an increase in the presence of the contrast agent released from the liposome at the desired site as the contents of the liposome are being released at the desired site;
(d) generating in real time a heating profile of the site of interest, wherein heating of an area to a temperature of at least T$_m$ is indicated by release of contrast agent.

20. The method of claim 19, wherein the thermosensitive liposome comprises a formulation selected from the group consisting of DPPC-PEG$_{2000}$, DPPC-DSPE-PEG$_{2000}$ (95:5, mol:mol); DPPC-MSPC-DSPE-PEG$_{2000}$ (90:10:4, mol:mol).

21. The method of claim 19, wherein the contrast agent is selected from the group consisting of Gd, Cu, Cr, Fe, Co, Er, Ni, Eu, Dy, Zn, Mg, Mo, Li, Ta, and Mn.

22. The method of claim 19, wherein the heating is by a method selected from the group consisting of contacting a heated material with the site of interest, applying RF or microwave energy to the site, applying ultrasonic energy to the site and applying a laser beam to the site.

23. The method of claim 19, wherein steps (a)-(c) are repeated a desired number of times.

24. The method of claim 23, wherein two or more thermosensitive liposomes are employed, each having a different T$_m$.

25. An in vivo method of monitoring the localization and distribution of a compound of interest to a desired site in an organism by magnetic resonance imaging, the method comprising:
(a) administering an envirosensitive liposome composition to a subject, the composition comprising:
(i) a contrast agent;
(ii) a compound of interest; and
(iii) an envirosensitive liposome encapsulating the contrast agent and the compound of interest; and
(b) monitoring in real time the localization and distribution of the compound of interest to a desired site by magnetic resonance imaging, wherein the monitoring comprises monitoring release of the contents of the liposome at the desired site by monitoring an increase in the presence of the contrast agent released from the liposome at the desired site as the contents of the liposome are being released at the desired site.

26. A method of monitoring the accumulation of a compound of interest at a desired site in vivo by magnetic resonance imaging, the method comprising:
(a) administering to a subject an envirosensitive liposome composition comprising:
(i) a contrast agent;
(ii) a compound of interest; and
(iii) an envirosensitive liposome encapsulating the contrast agent and the compound of interest; and
(b) monitoring in real time the accumulation of the compound of interest at a desired site by magnetic resonance imaging, wherein the monitoring comprises monitoring release of the contents of the liposome at the desired site by monitoring an increase in the presence of the contrast agent released from the liposome at the desired site as the contents of the liposome are being released at the desired site.

* * * * *